US011345654B2

(12) United States Patent
Lenzini

(10) Patent No.: US 11,345,654 B2
(45) Date of Patent: May 31, 2022

(54) POLYMORPHIC COMPOUNDS AND USES THEREOF

(71) Applicant: Navitor Pharmaceuticals, Inc., Cambridge, MA (US)

(72) Inventor: Silvia Lenzini, Verona (IT)

(73) Assignee: NAVITOR PHARMACEUTICALS, INC., Cambridge, MA (US)

( * ) Notice: Subject to any disclaimer, the term of this patent is extended or adjusted under 35 U.S.C. 154(b) by 76 days.

(21) Appl. No.: 16/662,517

(22) Filed: Oct. 24, 2019

(65) Prior Publication Data
US 2020/0131114 A1    Apr. 30, 2020

Related U.S. Application Data

(60) Provisional application No. 62/749,922, filed on Oct. 24, 2018.

(51) Int. Cl.
C07C 225/06 (2006.01)

(52) U.S. Cl.
CPC ........ C07C 225/06 (2013.01); C07B 2200/13 (2013.01)

(58) Field of Classification Search
CPC ............................ C07C 225/06; C07C 229/08
USPC ........................................................ 514/561
See application file for complete search history.

(56) References Cited

U.S. PATENT DOCUMENTS

| | | | |
|---|---|---|---|
| 4,346,110 | A | 8/1982 | Palfreyman et al. |
| 5,639,600 | A | 6/1997 | McGrath et al. |
| 6,458,781 | B1 | 10/2002 | Connor et al. |
| 7,087,648 | B1 | 8/2006 | McGrath |
| 7,390,799 | B2 | 6/2008 | Bruncko et al. |
| 8,138,347 | B2 | 3/2012 | Knight et al. |
| 10,100,066 | B2 | 10/2018 | Fetalvero et al. |
| 10,414,782 | B2 | 9/2019 | Fetalvero et al. |
| 10,752,644 | B2 | 8/2020 | Fetalvero et al. |
| 10,912,750 | B2 | 2/2021 | Salah et al. |
| 2003/0203900 | A1 | 10/2003 | Quibell |
| 2004/0110982 | A1 | 6/2004 | Anderson et al. |
| 2007/0082894 | A1 | 4/2007 | Burns et al. |
| 2010/0093706 | A1 | 4/2010 | Hauske |
| 2012/0219596 | A1 | 8/2012 | Limbach et al. |
| 2012/0225859 | A1 | 9/2012 | Burger et al. |
| 2012/0231993 | A1 | 9/2012 | Gazic Smilovic et al. |
| 2013/0116430 | A1 | 5/2013 | Fujiwara et al. |
| 2013/0296245 | A1 | 11/2013 | Li et al. |
| 2014/0186453 | A1 | 7/2014 | Zale et al. |
| 2015/0105386 | A1 | 4/2015 | Mack et al. |
| 2016/0137606 | A1 | 5/2016 | Bissantz et al. |
| 2017/0114080 | A1 | 4/2017 | Fetalvero et al. |
| 2017/0369435 | A1 | 12/2017 | Pourgholami et al. |
| 2018/0333381 | A1 | 11/2018 | Salah et al. |
| 2019/0240174 | A1 | 8/2019 | During |
| 2020/0079800 | A1 | 3/2020 | Fetalvero et al. |
| 2020/0131114 | A1 | 4/2020 | Lenzini |

FOREIGN PATENT DOCUMENTS

| | | |
|---|---|---|
| EP | 1389617 A1 | 2/2004 |
| WO | WO-1998008853 A1 | 3/1998 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078846 A1 | 7/2006 |
| WO | WO-2006117696 A2 | 11/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009114512 A1 | 9/2009 |
| WO | WO-2013142229 A1 | 9/2013 |
| WO | WO-2014127052 A1 | 8/2014 |
| WO | 2014201111 A1 | 12/2014 |
| WO | WO-2017070518 A1 | 4/2017 |
| WO | 2017083823 A1 | 5/2017 |
| WO | WO-2018200625 A1 | 11/2018 |
| WO | WO-2020086816 A1 | 4/2020 |

OTHER PUBLICATIONS

Abe et al., "Mammalian target of Rapamycin (mTOR) Activation Increases Axonal Growth Capacity of Injured Peripheral Nerves," The Journal of Biological Chemistry, vol. 285, No. 36, Sep. 3, 2010 (pp. 28034-28043).
Ali et al., "IL-15-PI3K-AKT-mTOR: A Critical Pathway in the Life Journey of Natural Killer Cells," Frontiers in Immunology, vol. 6, No. 355, Jul. 20, 2015 (9 pages).
Andrzejewska et al., "Cystinosin is a Component of the Vacuolar H+-ATPase-Ragulator-Rag Complex Controlling Mammalian Target of Rapamycin Complex 1 Signaling," Journal of the American Society of Nephrology, vol. 27, No. 6, Jun. 2016 (pp. 1678-1688).
Bar-Peled et al, "Regulation of mTORC1 by amino acids", Trends in Cell Biology, Jul. 2014, vol. 24, No. 7, pp. 400-406.
Bar-Peled et al., "A Tumor suppressor complex with GAP activity for the RAG GTPases that signal amino acid sufficiency to mTORC1," Science, vol. 340, No. 6136, May 2013 (1100-1106).
Bar-Peled et al., "An expanded Ragulator is a GEF for the rag GTPases that signal amino acid levels to mTORC1," Cell, vol. 150, No. 6, Sep. 2012 (pp. 1196-1208).
Berge et al., "Pharmaceutical Salts," Journal of Pharmaceutical Sciences, vol. 66, Jan. 1977 (pp. 1-19).
Bidinosti et al., "CLK2 inhibition ameliorates autistic features associated with SHANK3 deficiency," Science, vol. 351, No. 6278, Mar. 2016 (pp. 1199-1203).

(Continued)

Primary Examiner — Ana Z Muresan
(74) Attorney, Agent, or Firm — Dechert LLP; Andrea L. C. . Reid; Todd Macklin

(57) ABSTRACT

The present invention relates to compounds and methods useful for selectively modulating mTORC1 activity.

17 Claims, 11 Drawing Sheets

(56) References Cited

OTHER PUBLICATIONS

Bowling et al., "Antipsychotics Activate mTORC1-Dependent Translation to Enhance Neuronal Morphological Complexity," Science Signaling vol. 7, No. 308, Jan. 2014 (31 pages).
Brugarolas et al., "Regulation of mTOR function in response to hypoxia by REDD1 and the TSC1/TSC2 tumor suppressor complex," Genes & Development, vol. 18. Nov. 2004 (pp. 2893-2904).
Buckbinder et al., "Gene regulation by temperature-sensitive p53 mutants: identification of p53 response genes," Proceedings of the National Academy of Sciences of the United States of America, vol. 91, No. 22, Oct. 1994 (pp. 10640-10644).
Budanov et al., "The p53 target genes sestrin1 and sestrin2 connect genotoxic stress and mTOR signaling," Cell, vol. 134, No. 3, Aug. 2008 (pp. 451-460).
Buerger et al., "Localization of Rheb to the endomembrane is critical for its signaling function," Biochemical and Biophysical Research Communications, vol. 344, No. 3, Jun. 2006 (pp. 869-880).
Bull et al, "Conjugate additions of organocuprates to a 3-methylene-6-isopropyldiketopiperazine acceptor for the asymmetric synthesis of homochiral a-amino acids", J. Chem. Soc, Perkins Trans. 1, 2001, 3281-3287.
Bures et al, "Chiral imidazole derivatives synthesis from enentiopure N-protected a-amino acids", Asymmetry 16, Jan. 2005, pp. 1347-1354.
Cao et al., "Autophagy Is Disrupted in a Knock-in Mouse Model of Juvenile Neuronal Ceroid Lipofuscinosis," Journal of Biological Chemistry, vol. 281, No. 29, Jul. 2006 (pp. 20483-20493).
Cao et al., "Translational control of entrainment and synchrony of the suprachiasmatic circadian clock by mTOR/4E-BP1 signaling," Neuron, vol. 79, No. 4, Aug. 2013 (pp. 712-724).
CAS STN Abstract, RN 1555441-22-9 (Pub. Feb. 25, 2014).
CAS STN Abstract, RN 1698493-03-6 (Pub. May 5, 2015).
CAS STN Abstract, RN 1779709-85-1 (Pub. Jun. 14, 2015).
CAS STN Abstract, RN 1780718-09-3 (Pub. Jun. 15, 2015).
Chantranupong et al., "The Sestrins interact with GATOR2 to negatively regulate the amino-acid-sensing pathway upstream of mTORC1," Cell Reports, vol. 9, No. 1, Oct. 2014 (pp. 1-8).
Chauhan et al., "Muscle-specific regulation of the mTOR signaling pathway in MuSK antibody seropositive (MuSK+) experimental autoimmune Myasthenia gravis (EAMG)," Neuroscience Research, vol. 77, No. 1-2, Sep.-Oct. 2013 (pp. 102-109).
Chen et al., "Design, Synthesis, Activity, and Structurie of a Novel Class of Matrix Metalloproteinase Inhibitors containing a Heterocyclic P2-P3 Amide Bond Isotere", Bioorganic & Medicinal Chemistry Letters, 1996, vol. 6, No. 13, pp. 1601-1606.
Chi, "Regulation and function of mTOR signaling in T cell fate decisions," National Reviews Immunology, vol. 12, No. 5, Apr. 2012 (pp. 325-338).
Child et al., "Cardiac mTORC1 Dysregulation Impacts Stress Adaptation and Survival in Huntington's Disease," Cell Rep. 2018;23(4):1020-1033.
Ching et al., "mTOR dysfunction contributes to vacuolar pathology and weakness in valosin-containing protein associated inclusion body myopathy," Human Molecular Genetics, vol. 22, No. 6, Mar. 2013 (pp. 1167-1179).
Cuthbertson et al., "Anabolic signaling deficits underlie amino acid resistance of wasting, aging muscle," FASEB Journal, vol. 19, No. 3, Mar. 2005 (pp. 422-424).
Deboves et al, "A new route to hydrophobic amino acids using copper-promoted reactions of serine-derived organozinc reagents", J. Chem. Soc., Perkins Tran. 1,2000, pp. 4284-4292.
Delgoffe et al., "The mTOR kinase differentially regulates effector and regulatory T cell lineage commitment," Immunity, vol. 30, No. 6, Jun. 2009 (pp. 832-844).
Di Polo, "Dendrite pathology and neurodegeneration: focus on mTOR," Neural Regeneration Research, vol. 10, No. 4, Apr. 2015 (pp. 559-561).

Dibble et al., "TBC1D7 is a third subunit of the TSC1-TSC2 complex upstream of mTORC1m" Molecular Cell, vol. 47, No. 4, Aug. 2012 (pp. 535-546).
Efeyan et al., "Amino acids and mTORC1: from lysosomes to disease," Trends in Molecular Medicine, vol. 18, No. 9, Sep. 2012 (pp. 524-533).
Garami et al., "Insulin Activation of Rheb, a Mediator of mTOR/S6K/4E-BP Signaling, Is Inhibited by TSC1 and 2," Molecular cell, vol. 11, Jun. 2003 (pp. 1457-1466).
Gordon et al., "Regulation of muscle protein synthesis and the effects of catabolic states," International Journal of Biochemistry and Cell Biology, vol. 45, No. 10, Oct. 2013 (pp. 2147-2157).
Gurpur et al., "Valproic acid activates the PI3K/Akt/mTOR pathway in muscle and ameliorates pathology in a mouse model of Duchenne muscular dystrophy," The American Journal of Pathology, vol. 174, No. 3, Mar. 2009 (pp. 999-1008).
Ham et al., "Leucine as a treatment for muscle wasting: A critical review," Clinical Nutrition, vol. 33, No. 6, Dec. 2014 (pp. 937-945).
Hirose et al., "RagA is a functional homologue of S. cerevisiae Gtr1p involved in the Ran/Gsp1-GTPase pathway," Journal of Cell Science, vol. 111, Pt. 1, Jan. 1998 (pp. 11-21).
Howell et al., "A growing role for mTOR in promoting anabolic metabolism," Biochemical Society Transactions, vol. 41, No. 4, Jul. 2013 (pp. 906-912).
Ignácio et al., "New perspectives on the involvement of mTOR in depression as well as in the action of antidepressant drugs," British Journal of Clinical Pharmacology, vol. 82, No. 5, Nov. 2015 (pp. 1280-1290).
Inoki et al., "Rheb GTPase is a direct target of TSC2 Gap activity and regulates mTOR signaling," Genes & Development, vol. 17, No. 15, Aug. 2003 (pp. 1829-1834).
International Search Report and Written Opinion issued by the United States Patent and Trademark Office as International Searching Authority for International Application No. PCT/US2018/029288, dated Jul. 6, 2018 (13 pages).
Ito et al., "A medium-term rat liver bioassay for rapid in vivo detection of carcinogenic potential of chemicals," Cancer Science, vol. 94, No. 1, Jan. 2003 (pp. 3-8).
Ivanova et al., "Altered mTOR signalling in nephropathic cystinosis," Journal of Inherited Metabolic Disease, vol. 39, No. 3, May 2016 (pp. 457-464).
Kang et al., "mTORC1 phosphorylation sites encode their sensitivity to starvation and rapamycin," Science, vol. 341, No. 6144, Jul. 2013 (16 pages).
Katholnig et al., "Immune responses of macrophages and dendritic cells regulated by mTOR signaling," Biochemical Society Transactions, vol. 41, No. 4, Aug. 2013 (pp. 927-933).
Kim et al., "mTOR: a pharmacologic target for autophagy regulation," The Journal of Clinical Investigation, vol. 125, No. 1, Jan. 2015 (pp. 25-32).
Kim et al., "Nutrient Regulation of the mTOR Complex 1 Signaling Pathway," Molecules and Cells, vol. 35, No. 6, Jun. 2013 (pp. 463-473).
Kim et al., "Regulation of TORC1 by Rag GTPases in nutrient response," Nature, Cell Biology, vol. 10, No. 8, Jul. 2008 (pp. 935-945).
Kye et al., "SMN regulates axonal local translation via miR-183/mTOR pathway," Human Molecular Genetics, vol. 23, No. 23, Dec. 2014 (pp. 6318-6331).
Köhler et al., "Inflammation in Depression and the Potential for Anti-Inflammatory Treatment," Current Neuropharmacol. 2016;14(7):732-742.
Lambe et al., "Hypocretin (Orexin) Induces Calcium Transients in Single Spines Postsynaptic to Identified Thalamocortical Boutons in Prefrontal Slice," Neuron, vol. 40, No. 1, Sep. 2003 (pp. 139-150).
Laplante et al., "mTOR signaling in growth control and disease," Cell, vol. 149, No. 2, Apr. 2012 (pp. 274-293).
Lee et al., "Platelets Support Extracellular Sialylation by Supplying the Sugar Donor Substrate," Journal of Biological Chemistry, vol. 289, No. 13, Mar. 2014 (pp. 8742-8748).
Lee et al., "reinstating aberrant mTORC1 activity in Huntington's disease mice improves disease phenotypes," Neuron, vol. 85, No. 2, Jan. 2015 (pp. 303-315).

(56) References Cited

OTHER PUBLICATIONS

Leger et al., "Atrogin-1, MuRF1, and FoXO, as well as phosphorylated GSK-3beta and 4E-BP1 are reduced in skeletal muscle of chronic spinal cord-injured patients," Muscle Nerve, vol. 40, No. 1, Jul. 2009 (pp. 69-78).
Li et al., "Glutamate N-methyl-D-aspartate receptor antagonists rapidly reverse behavioral and synaptic deficits caused by chronic stress exposure," Biological Psychiatry, vol. 69, No. 8, Apr. 2011 (pp. 754-761).
Li et al., "mTOR-dependent synapse formation underlies the rapid antidepressant effects of NMDA antagonists," Science, vol. 329, No. 5994, Aug. 2010 (pp. 959-964).
Liebau et al., "Dysregulated Autophagy Contributes to Podocyte Damage in Fabry's Disease," PLoS One, vol. 8, No. 5, May 2013 (10 pages).
Lin et al., "Activation of mTOR Ameliorates Fragile X Premutation rCGG Repeat-Mediated Neurodegeneration," PLOS One, vol. 8, No. 4, e62572, Apr. 2013 (pp. 1-8).
Liu et al., "GLYX-13 Produces Rapid Antidepressant Responses with Key Synaptic and Behavioral Effects Distinct from Ketamine," Neuropharmacology, vol. 42, No. 6, May 2017 (pp. 1231-1242).
Liu et al., "Hypocretins (Orexins) Regulate Serotonin Neurons in the Dorsal Raphe Nucleus by Excitatory Direct and Inhibitory Indirect Actions," Journal of Neuroscience, vol. 22, No. 21, Nov. 2002 (pp. 9453-9464).
Long et al., "Rheb Binds and Regulates the mTOR Kinase," Current Biology, vol. 15, No. 8, Apr. 2005 (pp. 702-713).
Love, "Demyelinating diseases," The Journal of Clinical Pathology, vol. 59, No. 11, Nov. 2006 (pp. 1151-1159).
Macovei et al, "Polyclonal antibodies: a cheap and efficient tool for screening of enantioselective catalysts", Chern. Dommun, 2012, vol. 48, pp. 4411-4413.
Malkesman et al., "The female urine sniffing test: a novel approach for assessing reward-seeking behavior in rodents," Biological Psychiatry, vol. 67, No. 9, May 2010 (pp. 864-871).
Manzi and Wasko, "Inflammation-mediated rheumatic diseases and atherosclerosis," Annals of the Rheumatic Diseases, vol. 59, No. 5, May 2000 (pp. 321-325).
McVey et al., "CHO cells knocked out for TSC2 display an improved productivity of antibodies underfed batch conditions," Biotechnology and Bioengineering, vol. 113, No. 9, Sep. 2016 (pp. 1942-1952).
Nakamura et al., "Role of the mTOR complex 1 pathway in the in vivo maintenance of the intestinal mucosa by oral intake of amino acids," Geriatric & Gerontology International, vol. 12, No. 1, Jan. 2012 (pp. 131-139).
Napolitano et al., "Impairment of chaperone-mediated autophagy leads to selective lysosomal degradation defects in the lysosomal storage disease cystinosis," EMBO Molecular Medicine, vol. 7, No. 2, Feb. 2015 (pp. 158-174).
Nelson et al., "Autophagy-lysosome pathway associated neuropathology and axonal degeneration in the brains of alpha-galactosidase A-deficient mice," Acta Neuropathologica Communications, vol. 2, No. 20, Feb. 2014 (pp. 1-15).
No Author, "substance Record for SID 219681321," PubChem, NIH U.S. National Library of Medicine, National Center for Biotechnology Information, retrieved only at <https://pubchem.ncbi.nlm.nih.gov/substance/219681321#section=Top> accessed Nov. 22, 2016 (6 pages).
No Author, "Substance Record for SID 4757389," PubChem, NIH U.S. National Library of Medicine, National Center for Biotechnology Information, retrieved only at <https://pubchem.ncbi.nlm.nih.gov/substance/4757389#section=Top> accessed Feb. 16, 2017 (5 pages).
No Author, "Substance Record for SID 8685219," PubChem, NIH U.S. National Library of Medicine, National Center for Biotechnology Information, retrieved only at <https://pubchem.ncbi.nlm.nih.gov/substance/8685219/version/1> accessed Nov. 22, 2016, (7 pages).
Nobukuni et al., "Amino acids mediate mTOR/raptor signaling through activation of class 3 phosphatidylinositol 3OH-kinase," Proceedings of the National Academy of Sciences of the United States of America, vol. 102, No. 40, Oct. 2005 (pp. 14238-14243).
Norrmen et al., "mTORC1 controls PNS myelination along the mTORC1-RXR-SREBP-lipid biosynthesis axis in Schwann cells," Cell Reports, vol. 9, No. 2, Oct. 2014 (pp. 646-660).
Novarino et al., "Mutation in BCKD-kinase Lead to a Potentially Treatable Form of Autism with Epilepsy," Science, vol. 338, No. 6105, Sep. 2012 (pp. 394-397).
O'Brien et al., "Regulation of T-cell survival and mitochondrial homeostasis by TSC1," European Journal of immunology, vol. 41, No. 11, Nov. 2011 (pp. 3361-3370).
Panchaud et al., "Amino Acid Deprivation Inhibits TORC1 Through a GTPase-Activating Protein Complex for the Rag Family GTPase Gtr1," Science Signaling, vol. 6, No. 277, May 2013 (p. ra42).
Park et al., "TSC1 regulates the balance between effector and regulatory T cells," The Journal of Clinical Investigation, vol. 123, No. 12, Dec. 2013 (pp. 5165-5178).
Pasiakos et al., "Leucine-enriched essential amino acid supplementation during moderate steady state exercise enhances postexercise muscle protein synthesis," The American Journal Clinical Nutrition, vol. 94, No. 3, Sep. 2011 (pp. 809-818).
Payne et al., "L-Leucine improves the anemia and developmental defects associates with Diamond-Blackfan anemia and del(5q) MDS by activating the mTOR pathway," Blood, vol. 120, No. 11, Sep. 2012 (pp. 2214-2224).
PCT International Search Report and Written Opinion from PCT/US2020/058475 dated Feb. 1, 2021.
Pearce et al., "Action of BTN1, the yeast orthologue of the gene mutated in Batten disease," Nature, Genetics, vol. 22, No. 1, May 1999 (pp. 55-58).
Pedroso et al., "Reviewing the Effects of L-Leucine Supplementation in the Regulation of Food Intake, energy Balance, and Glucose Homeostasis," Nutrients, vol. 7, No. 5, May 2015 (pp. 3914-3937).
Peeters et al., "PA26 is a candidate gene for heterotaxia in humans: identification of a novel PA26-related gene family in human and mouse," Human Genetics, vol. 112, No. 5-6, Feb. 2003 (pp. 573-580).
Peng et al., "Sestrins function as guanine nucleotide dissociation inhibitors for Rag GTPases to control mTORC1 signaling," vol. 159, No. 1, Sep. 2014 (pp. 122-133).
Pollizzi et al., "mTORC1 and mTORC2 selectively regulate CD8+ T cell differentiation," The Journal of Clinical Investigation, vol. 125, No. 5, May 2015 (pp. 2090-2108).
Punzo et al., "Stimulation of the insulin/,TOR pathway delays cone death in a mouse model of retinitis pigmentosa," Nature Neuroscience, vol. 12, No. 1, Jan. 2009 (pp. 44-52).
Rennie, "Anabolic resistance: the effects of aging, sexual dimorphism, and immobilization on human muscle protein turnover," Applied Physiology, Nutrition, and Metabolism, vol. 34, No. 3, Jun. 2009 (pp. 377-381).
Roccio et al., "Regulation of the small GTPase Rheb by amino acids," Oncogene, vol. 25, No. 5. Feb. 2006 (pp. 657-664).
Saito et al., "Novel Role of the Small GTPase Rheb: Its Implication in Endocytic Pathway Independent of the Activation of Mammalian Target of Rapamycin," Journal of Biochemistry, vol. 137, No. 3, Mar. 2005 (pp. 423-430).
Sancak et al., "Ragulator-Rag complex targets mTORCI to the lysosomal surface and is necessary for its activation by amino acids," Cell, vol. 141, No. 2, Apr. 2010 (pp. 290-303).
Sancak et al., "The Rag GTPases bind raptor and mediate amino acid signaling to mTORC1," Science, vol. 320, No. 5882, Jun. 2008 (pp. 1496-1501).
Saucedo et al., "Rheb promotes cell growth as a component of the insulin/TOR signalling network," Nature, Cell Biology, vol. 5, No. 6, Jun. 2003 (pp. 566-571).
Schürmann et al., "Cloning of a Novel Family of Mammalian GTP-binding Proteins (RagA, RagBs, RagB1) with Remote Similarity to the Ras-related GTPases ," Journal of Biological Chemistry, vol. 270, No. 48, Dec. 1995 (pp. 28982-28988).

(56) References Cited

OTHER PUBLICATIONS

Sekiguchi et al., "Novel G Proteins, Rag C and Rag D, Interact with GTP-binding Proteins, Rag A and Rag B," Journal of Biological Chemistry, vol. 276, No. 10, Mar. 2001 (pp. 7246-7257).
Smith et al., "The Tuberous Sclerosis Protein TSC2 Is Not Required for the Regulation of the Mammalian Target of Rapamycin by Amino Acids and Certain Cellular Stresses," Journal of Biological Chemistry, vol. 280, No. 19, May 2005 (pp. 18717-18727).
Song et al., "A simple method for preparation of N-mono- and N,N-di-alkylated a-amino acids", Tetrahedron Letters, vol. 41, 2000, pp. 8225-8230.
Song et al., "mTOR Attenuates the Inflammatory Response in Cardiomyocytes and Prevents Cardiac Dysfunction in Pathological Hypertrophy," The American Journal of Physiology Cell Physiology, vol. 299, No. 6, Sep. 2010 (pp. C1256-C1266).
Stein et al., "Protein kinetics during and after long-duration spaceflight on MIR," The American Journal of Physiology Endocrinology Metabolism, vol. 276, No. 6 Part 1, Jun. 1999 (pp. E1014-E1021).
Stocker et al., "Rheb is an essential regulator of S6K in controlling cell growth in *Drosophila*," Nature, Cell Biology, vol. 5, No. 6, Jun. 2003 (pp. 559-565).
Takikita et al., "Pertubed myelination process of premyelinating oligodendrocyte in Niemann-Pick type C mouse," The Journal Neuropathology and Experimental Neurology, vol. 63, No. 6, Jun. 2004 (pp. 660-673).
Tee et al., "Tuberous sclerosis complex-1 and -2 gene products function together to inhibit mammalian target of rapamycin (mTOR)-mediated downstream signaling," Proceedings of the National Academy of Sciences of the United States of America, vol. 99, No. 21, Oct. 2002 (pp. 13571-13576).
Tsun et al., "The foiliculin tumor suppressor is a GAP for the RagC/D GTPases that signal amino acid levels to mTORC1," Molecular Cell, vol. 52, No. 4, Nov. 2013 (pp. 495-505).
Tyler et al., "Activation of the mammalian target of rapamycin (mTOR) is essential for oligodendrocyte differentiation," The Journal of Neuroscience, vol. 29, No. 19, May 13, 2009 (pp. 6367-6378).
Vergarajauregui et al., "Autophagic dysfunction in mucolipidosis type IV patients," Human Molecular Genetics, vol. 17, No. 17, Sep. 2008 (pp. 2723-2737).
Wang et al., "Lysosomal amino acid transporter SLC38A9 signals arginine sufficiency to mTORCI," Science, vol. 347, No. 6218, Jan. 2015 (pp. 188-194).
Wang et al., "The amino acid transporter SLC38A9 is a key component of a lysosomal membrane complex that signals arginine sufficiency to mTORC1," Science, vol. 347, No. 6218, Jan. 2015 (pp. 188-194).
Wang et al., "Tuberous sclerosis 1 (Tsc1)-dependent metabolic checkpoint controls development of dendritic cells," Proceedings of the National Academy of Science U.S.A., vol. 110, No. 50, Dec. 2013 (pp. E4894-E4903).
Warner-Schmidt and Duman, "VEGF is an essential mediator of the neurogenic and behavioral actions of antidepressants," Proceedings of the National Academy of Sciences of the United States of America, vol. 104, No. 11, Mar. 2007 (pp. 4647-4652).
Wolfson et al., "Sestrin2 is a leucine sensor forthe mTORC1 pathway," Science, vol. 351, No. 6268, Jan. 2016 (pp. 43-48).
Wong et al., "*Drosophila* TRPML is Required ForTORC1 Activation," Current Biology, vol. 22, No. 17, Sep. 2012 (pp. 1616-1621).
Xu et al., "A Mental Retardation-linked Nonsense Mutation in Cereblon Is Rescued by Proteasome Inhibition," Journal of Biological Chemistry, vol. 288, No. 41, Oct. 2013 (pp. 29573-29585).
Xu et al., "Improved transcription and translation with L-leucine stimulation of mTORC1 in Roberts syndrome," BMC Genomics, vol. 17, No. 25, No. Month Listed 2016 (18 pages).

Yang et al., "Reduced Excitatory Neurotransmission and Mild Autism-Relevant Phenotypes in Adolescent Shank3 Null Mutant Mice," Journal of Neuroscience, vol. 32, No. 19, May 2012 (pp. 6525-6541).
Yang et al., "The tumor suppressor Tscl enforces quiescence of naive T cells to promote immune homeostasis and function," Nature Immunology, vol. 12, No. 9, Jul. 2011 (pp. 888-897).
Ye et al., "Chemical aminoacylation of tRNAs with fluorinated amino acids for in vitro protein mutagenesis", Bellstein Journal of Organic Chemistry, 2010, vol. 6, No. 40, pp. 1-6.
Zoncu et al., "mTORC1 senses lysosomal amino acids through an inside-out mechanism that requires the vacuolar H(+)-ATPase," Science, vol. 344, No. 6056, Nov. 2011 (pp. 678-683).
Andrzejewska et al., 2016, "Cystinosin is a Component of the Vacuolar H+-ATPase-Ragulator-Rag Complex Controlling Mammalian Target of Rapamycin Complex 1 Signaling," J. Am. Soc. Nephrol. 27(6):11678-1688.
Bidinosti et al., 2016, "CLK2 inhibition ameliorates autistic features associated with SHANK3 deficiency," Science 351 (6278):11199-1203.
Cao et al., 2006, "Autophagy is disrupted in a knock-in mouse model of juvenile neuronal ceroid lipofuscinosis," J. Biol. Chem. 281(29):120483-20493.
Fossale et al., 2004, "Membrane trafficking and mitochondrial abnormalities precede subunit c deposition in a cerebellar cell model of juvenile neuronal ceroid lipofuscinosis," BMC Neurosci. 5(1):157.
Howell et al., 2013, "A growing role for mTOR in promoting anabolic metabolism," Biochem. Soc. Trans. 41(4):1906-912.
Ignácio et al., 2015, "New perspectives on the involvement of mTOR in depression as well as in the action of antidepressant drugs," Br. J. Clin. Pharmacol. 82(5):11280-1290.
Ivanova et al., 2016, "Altered mTOR signalling in nephropathic cystinosis," J. Inherit. Metab. Dis. 39(3):1457-464.
Kim et al., 2013, "Nutrient Regulation of the mTOR Complex 1 Signaling Pathway," Mol. Cells 35(6):1463-473.
Laplante & Sabatini, 2012, "mTOR signaling in growth control and disease," Cell 149(2):1274-293.
Lee et al., 2014, "Functional effects of a pathogenic mutation in Cereblon (CRBN) on the regulation of protein synthesis via the AMPK-mTOR cascade," J Biol Chern 289(34):123343-23352.
Liebau et al., 2013, "Dysregulated Autophagy Contributes to Podocyte Damage in Fabry's Disease," PLoS One 8(5):e63506.
Napolitano et al., 2015, "Impairment of chaperone-mediated autophagy leads to selective lysosomal," EMBO Mol. Med. 7(2):158-174.
Nelson et al., 2014,"Autophagy-lysosome pathway associated neuropathology and axonal degeneration in the brains of alpha-galactosidase A-deficient mice," Acta Neuropathol. Commun 2:20.
Novarino et al., 2012, "Mutations in BCKD-kinase lead to a potentially treatable form of autism with epilepsy," Science 338(6105):394-397.
PCT International Search Report and Written Opinion from PCT/US2019/057815 dated Jan. 6, 2020.
Pearce et al., 1999, "Action of BTN1, the yeast orthologue of the gene mutated in Batten disease," Nat. Genet. 22(1):55-58.
Tarlungeanu et al., 2016, "Impaired Amino Acid Transport at the Blood Brain Barrier Is a Cause of Autism Spectrum Disorder," Cell 167(6):1481-1494.
Vergarajauregui et al., 2008, "Autophagic dysfunction in mucolipidosis type IV patients," Hum. Mol. Genet. 17(17):2723-2737.
Wong et al., 2012, "Drosophila TRPML is required for TORC1 activation," Curr. Biol. 22(17):1616-21.
Xu et al., 2013, "A mental retardation-linked nonsense mutation in cereblon is rescued by proteasome inhibition," J. Biol. Chem. 288(41):29573-29585.
Yang et al., 2012, "Reduced excitatory neurotransmission and mild autism-relevant phenotypes in adolescent Shank3 null mutant mice," J. Neurosci. 32(19):6525-6541.

POLYMORPHIC COMPOUNDS AND USES THEREOF

TECHNICAL FIELD OF THE INVENTION

The present invention relates to compounds and methods useful for modulating mTORC1 activity. The present invention relates to compounds and methods useful for selectively modulating mTORC1 activity. The present invention relates to compounds and methods useful for activating mTORC1. The invention also provides pharmaceutically acceptable compositions comprising compounds of the present invention and methods of using said compositions in the treatment of various disorders.

BACKGROUND OF THE INVENTION

The mechanistic target of rapamycin complex 1 (mTORC1) protein kinase is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell et al., (2013) Biochemical Society transactions 41, 906-912; Kim et al., (2013) Molecules and cells 35, 463-473; Laplante and Sabatini, (2012) Cell 149, 274-293).

There is urgent and compelling unmet medical need for more effective treatments for diseases, disorders or conditions associated with mTORC1.

SUMMARY OF THE INVENTION

It has now been found that compounds of this invention, and pharmaceutically acceptable compositions thereof, are effective as mTORC1 modulators. Such compounds are represented by the chemical structure below, denoted as compound A:

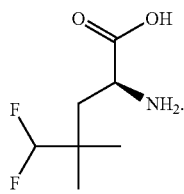

Compounds of the present invention, and pharmaceutically acceptable compositions thereof, are useful for treating a variety of diseases, disorders or conditions, including those described herein. Compounds of the present invention, and pharmaceutically acceptable compositions thereof, are useful for treating a variety of diseases, disorders or conditions, associated with mTORC1. Such diseases, disorders, or conditions include diabetes, epilepsy, neurodegeneration, immune response, suppressed skeletal muscle growth, and cellular proliferative disorders (e.g., cancer) such as those described herein.

DETAILED DESCRIPTION OF THE INVENTION

Figure 1:
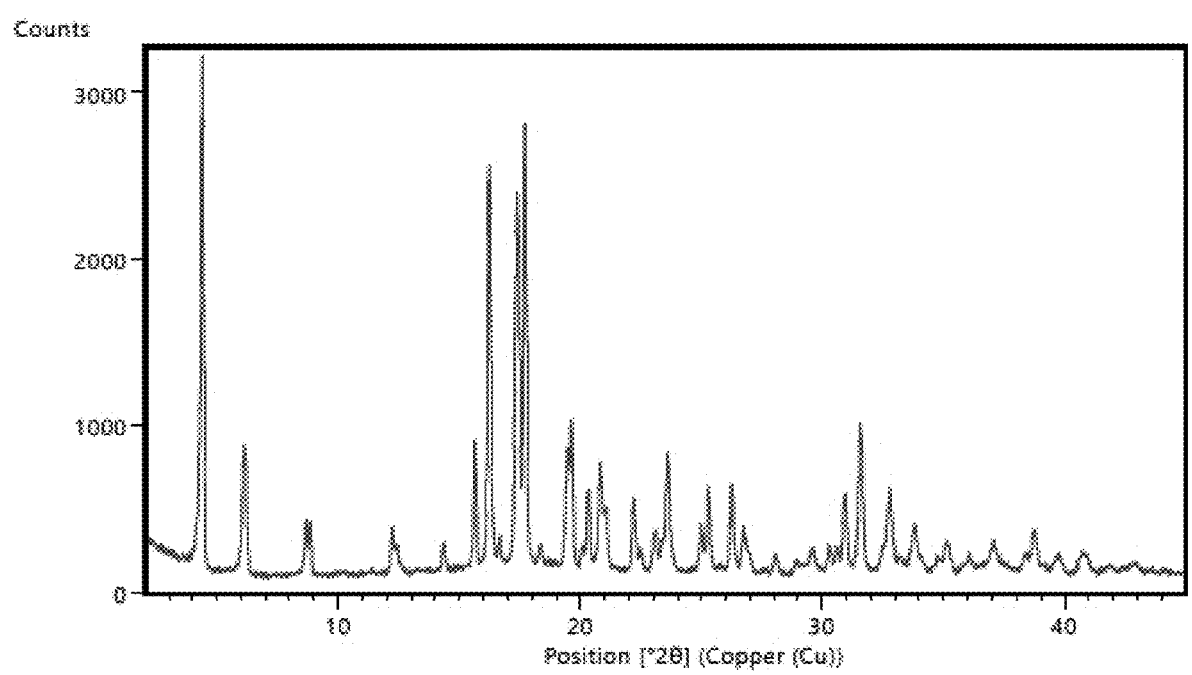
FIG. 1 depicts an XRPD pattern of Form A of compound A.

General Description of Certain Aspects of the Invention

U.S. Pat. No. 10,100,066 ("the '066 patent") filed Oct. 21, 2016 as U.S. patent application Ser. No. 15/331,362 and published as U.S. Pat. App. Pub. No. U.S. 2017/0114080 ("the '080 publication"), the entirety of each is incorporated herein by reference, describe certain mTORC1 modulating compounds. Such compounds include compound A:

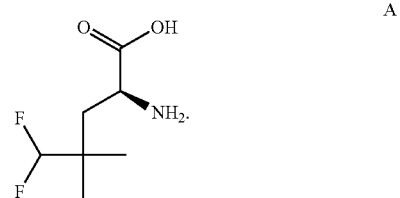

Compound A, ((S)-2-amino-5,5-difluoro-4,4-dimethylpentanoic acid), is designated as compound I-90 in the '066 patent and the synthesis of compound A is described in detail at Example 90 of the '066 patent.

It would be desirable to provide a solid form of compound A (e.g., as a free base thereof or hydrate thereof) that imparts characteristics such as improved aqueous solubility, stability and ease of formulation. Accordingly, the present invention provides free base forms and hydrate forms of compound A.

Free Base Forms of Compound A

It is contemplated that compound A can exist in a variety of physical forms. For example, compound A can be in solution, suspension, or in solid form. In certain embodiments, compound A is in solid form. When compound A is in solid form, said compound may be amorphous, crystalline, or a mixture thereof. Exemplary solid forms are described in more detail below.

In some embodiments, the present invention provides a form of compound A substantially free of impurities. As used herein, the term "substantially free of impurities" means that the compound contains no significant amount of extraneous matter. Such extraneous matter may include different forms of compound A, residual solvents, or any other impurities that may result from the preparation of, and/or isolation of, compound A. In certain embodiments, at least about 95% by weight of a form of compound A is present. In still other embodiments of the invention, at least about 99% by weight of a form of compound A is present.

According to one embodiment, a form of compound A is present in an amount of at least about 97, 97.5, 98.0, 98.5, 99, 99.5, 99.8 weight percent where the percentages are based on the total weight of the composition. According to another embodiment, a form of compound A contains no more than about 3.0 area percent HPLC of total organic impurities and, in certain embodiments, no more than about 1.5 area percent HPLC total organic impurities relative to the total area of the HPLC chromatogram. In other embodiments, a form of compound A contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound A is also meant to include all tautomeric forms of compound A. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound A can exist in a variety of solid forms. Exemplary such forms include polymorphs such as those described herein.

As used herein, the term "polymorph" refers to the different crystal structures into which a compound, or a salt or solvate thereof, can crystallize.

In certain embodiments, compound A is a crystalline solid. In other embodiments, compound A is a crystalline solid substantially free of amorphous compound A. As used herein, the term "substantially free of amorphous compound A" means that the compound contains no significant amount of amorphous compound A. In certain embodiments, at least about 95% by weight of crystalline compound A is present. In still other embodiments of the invention, at least about 99% by weight of crystalline compound A is present.

It has been found that compound A can exist in at least three distinct polymorphic forms. In certain embodiments, the present invention provides a polymorphic form of compound A referred to herein as Form A. In certain embodiments, the present invention provides a polymorphic form of compound A referred to herein as Form B. In certain embodiments, the present invention provides a polymorphic form of compound A referred to herein as Form C.

In some embodiments, compound A is amorphous. In some embodiments, compound A is amorphous, and is substantially free of crystalline compound A.

Form A of Compound A

In some embodiments, Form A of compound A has at least 1, 2, 3, 4 or 5 spectral peak(s) selected from the peaks listed in Table 1 below.

TABLE 1

XRPD Peak Positions for Form A of Compound A

| Pos. [°2θ][1] | d-spacing [Å] | Rel. Int. [%] |
|---|---|---|
| 4.4 | 19.96942 | 100.00 |
| 6.1 | 14.45004 | 25.45 |
| 6.2 | 14.21554 | 22.07 |
| 8.7 | 10.20120 | 11.00 |
| 8.8 | 10.00741 | 10.76 |
| 12.2 | 7.23011 | 9.66 |
| 14.4 | 6.16658 | 6.34 |
| 15.6 | 5.66238 | 26.43 |
| 16.2 | 5.45686 | 81.29 |
| 16.7 | 5.31669 | 7.92 |
| 17.3 | 5.11234 | 68.23 |
| 17.5 | 5.07462 | 64.89 |
| 17.7 | 5.00663 | 88.87 |
| 18.4 | 4.82874 | 5.82 |
| 19.4 | 4.56431 | 23.79 |
| 19.6 | 4.52142 | 30.99 |
| 20.1 | 4.42642 | 5.20 |
| 20.3 | 4.37616 | 15.93 |
| 20.8 | 4.27126 | 21.94 |
| 21.1 | 4.21293 | 12.75 |
| 22.2 | 4.00638 | 14.90 |
| 22.5 | 3.95102 | 4.50 |
| 23.1 | 3.84773 | 8.84 |
| 23.6 | 3.76897 | 23.73 |
| 25.0 | 3.56717 | 9.90 |
| 25.3 | 3.52477 | 17.35 |
| 26.2 | 3.39632 | 17.70 |
| 26.7 | 3.33700 | 8.63 |
| 26.9 | 3.31631 | 5.15 |
| 28.1 | 3.17794 | 3.60 |
| 28.9 | 3.08581 | 2.40 |
| 29.6 | 3.01622 | 4.77 |
| 30.3 | 2.95375 | 5.72 |
| 30.6 | 2.92314 | 5.39 |
| 30.9 | 2.89490 | 12.46 |
| 31.0 | 2.88869 | 14.44 |
| 31.6 | 2.83502 | 29.78 |
| 32.8 | 2.73158 | 17.12 |
| 33.8 | 2.65090 | 9.60 |
| 34.7 | 2.58456 | 3.04 |
| 35.1 | 2.55777 | 5.93 |
| 36.1 | 2.49100 | 4.11 |
| 37.1 | 2.42595 | 6.69 |
| 38.3 | 2.34795 | 4.11 |
| 38.7 | 2.32505 | 8.85 |
| 39.8 | 2.26429 | 3.32 |
| 40.9 | 2.20715 | 3.73 |
| 41.8 | 2.15870 | 1.37 |
| 42.9 | 2.10893 | 1.92 |
| 43.6 | 2.07629 | 0.89 |

[1] In this and all subsequent tables, the position 2θ is within ±0.2.

In some embodiments, Form A of compound A is characterized in that it has one or more peaks in its X-ray powder diffraction pattern selected from those at about 4.4, about 16.2 and about 17.7 degrees 2-theta. In some embodiments, Form A of compound A is characterized in that it has two or more peaks in its X-ray powder diffraction pattern selected from those at about 4.4, about 16.2 and about 17.7 degrees 2-theta. In some embodiments, Form A of compound A is characterized in that it has all three peaks in its X-ray powder diffraction pattern selected from those at about 4.4, about 16.2 and about 17.7 degrees 2-theta. As used herein, the term "about", when used in reference to a degree 2-theta value refers to the stated value±0.2 degree 2-theta.

In certain embodiments, the X-ray powder diffraction pattern is substantially similar to the XRPD provided in FIG. 1.

Methods for preparing Form A of compound A are described infra.

Form B of Compound A

In some embodiments, Form B of compound A has at least 1, 2, 3, 4 or 5 spectral peak(s) selected from the peaks listed in Table 2 below.

TABLE 2

XRPD Peak Positions for Form B of Compound A

| Pos. [°2θ][1] | d-spacing [Å] | Rel. Int. [%] |
|---|---|---|
| 5.0 | 17.79192 | 56.67 |
| 5.6 | 15.84291 | 27.64 |
| 6.2 | 14.16750 | 56.60 |
| 7.3 | 12.11387 | 1.29 |
| 8.5 | 10.39085 | 15.91 |
| 11.2 | 7.93259 | 4.90 |
| 12.5 | 7.09034 | 5.45 |
| 13.5 | 6.54504 | 6.60 |
| 14.9 | 5.94738 | 7.79 |
| 15.2 | 5.81272 | 57.62 |
| 15.8 | 5.62075 | 25.30 |
| 15.9 | 5.55836 | 28.07 |
| 16.3 | 5.42768 | 7.96 |
| 16.7 | 5.29724 | 28.92 |
| 17.2 | 5.16239 | 47.38 |
| 17.5 | 5.08070 | 100.00 |
| 17.8 | 4.99676 | 55.49 |
| 18.6 | 4.77136 | 51.51 |
| 18.9 | 4.70370 | 12.08 |
| 20.1 | 4.42463 | 4.58 |
| 20.5 | 4.33118 | 42.34 |
| 20.8 | 4.27546 | 20.03 |
| 21.0 | 4.22175 | 16.50 |
| 21.8 | 4.07643 | 14.81 |
| 22.3 | 3.98920 | 20.06 |
| 22.8 | 3.89446 | 20.78 |
| 23.9 | 3.72765 | 6.29 |
| 24.0 | 3.70144 | 7.86 |
| 24.4 | 3.64301 | 13.63 |
| 25.1 | 3.54860 | 14.27 |
| 25.5 | 3.49056 | 16.11 |
| 25.7 | 3.46934 | 13.54 |
| 27.3 | 3.26880 | 6.08 |
| 28.2 | 3.16194 | 18.51 |
| 28.6 | 3.11881 | 2.62 |
| 30.2 | 2.95839 | 5.60 |
| 30.7 | 2.90800 | 15.69 |
| 31.5 | 2.84376 | 2.75 |
| 31.8 | 2.81261 | 14.16 |
| 32.3 | 2.77431 | 25.65 |
| 32.9 | 2.72628 | 3.13 |
| 33.2 | 2.69691 | 4.85 |
| 33.5 | 2.67365 | 7.08 |
| 34.1 | 2.62624 | 6.69 |
| 34.7 | 2.58345 | 6.04 |
| 35.8 | 2.50835 | 6.32 |
| 36.4 | 2.46997 | 2.39 |
| 36.9 | 2.43571 | 2.52 |
| 37.9 | 2.37271 | 4.64 |
| 38.8 | 2.32345 | 2.55 |
| 40.0 | 2.25278 | 6.92 |
| 41.1 | 2.19506 | 0.97 |
| 41.7 | 2.16684 | 2.73 |
| 42.5 | 2.12870 | 1.74 |
| 43.6 | 2.07769 | 2.05 |
| 44.3 | 2.04573 | 0.93 |

[1]In this and all subsequent tables, the position 2θ is within ± 0.2.

In some embodiments, Form B of compound A is characterized in that it has one or more peaks in its X-ray powder diffraction pattern selected from those at about 5.0, about 15.2 and about 17.5 degrees 2-theta. In some embodiments, Form B of compound A is characterized in that it has two or more peaks in its X-ray powder diffraction pattern selected from those at about 5.0, about 15.2 and about 17.5 degrees 2-theta. In some embodiments, Form B of compound A is characterized in that it has all three peaks in its X-ray powder diffraction pattern selected from those at about 5.0, about 15.2 and about 17.5 degrees 2-theta.

Figure 4:
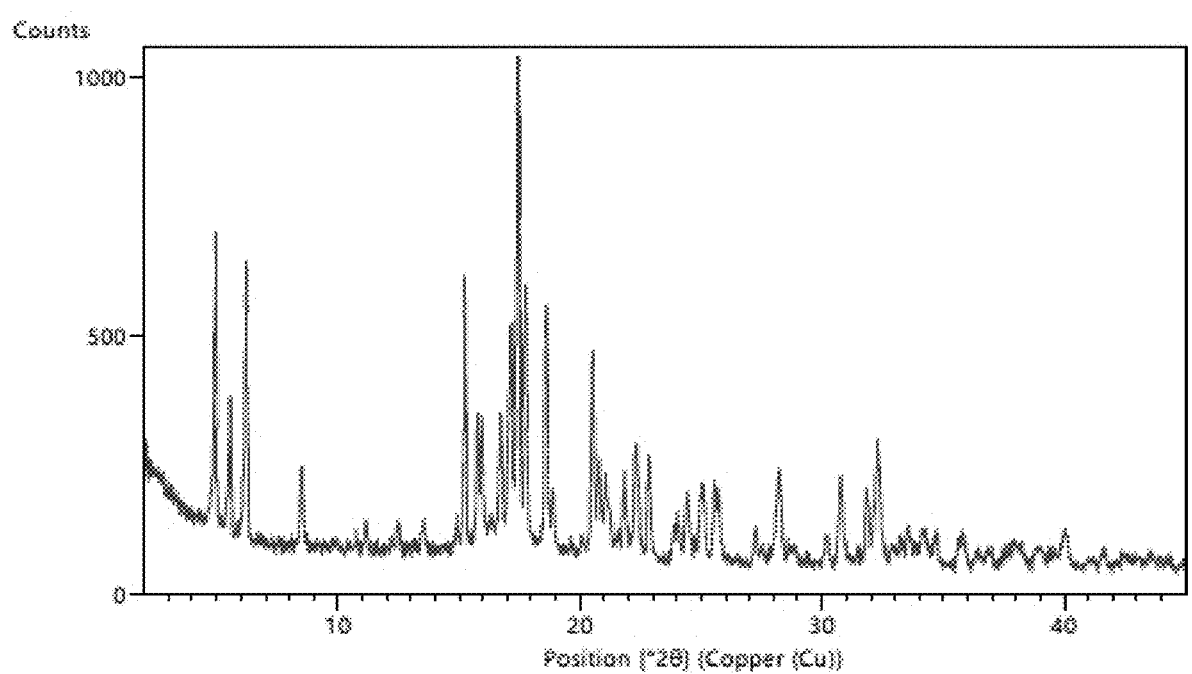
FIG. 4 depicts an XRPD pattern of Form B of compound A.

In certain embodiments, the X-ray powder diffraction pattern is substantially similar to the XRPD provided in FIG. 4.

Methods for preparing Form B of compound A are described infra.

Form C of Compound A

In some embodiments, Form C of compound A has at least 1, 2, 3, 4 or 5 spectral peak(s) selected from the peaks listed in Table 3 below.

TABLE 3

XRPD Peak Positions for Form C of Compound A

| Pos. [°2θ][1] | d-spacing [Å] | Rel. Int. [%] |
|---|---|---|
| 7.0 | 12.62256 | 100.00 |
| 9.0 | 9.84758 | 0.61 |
| 12.7 | 6.95918 | 1.03 |
| 13.7 | 6.45156 | 1.18 |
| 14.0 | 6.31699 | 1.35 |
| 14.6 | 6.06056 | 1.01 |
| 15.2 | 5.82154 | 12.92 |
| 16.1 | 5.50413 | 26.10 |
| 16.3 | 5.44751 | 81.62 |
| 17.1 | 5.19272 | 8.97 |
| 18.1 | 4.90525 | 15.44 |
| 18.6 | 4.76865 | 13.36 |
| 19.3 | 4.59577 | 19.92 |
| 19.5 | 4.54539 | 23.36 |
| 20.6 | 4.31976 | 8.55 |
| 21.1 | 4.20763 | 13.52 |
| 22.2 | 3.99811 | 6.29 |
| 22.7 | 3.92968 | 2.23 |
| 23.2 | 3.83507 | 4.95 |
| 24.1 | 3.68762 | 4.52 |
| 24.7 | 3.60895 | 3.78 |
| 25.1 | 3.54244 | 18.19 |
| 25.6 | 3.47585 | 2.91 |
| 26.1 | 3.40952 | 1.00 |
| 27.2 | 3.27682 | 2.65 |
| 27.7 | 3.22347 | 2.42 |
| 28.3 | 3.15590 | 2.86 |
| 30.0 | 2.98309 | 1.88 |
| 30.7 | 2.90868 | 2.28 |
| 31.5 | 2.84434 | 1.49 |
| 32.6 | 2.74884 | 6.13 |
| 32.8 | 2.72865 | 4.39 |
| 33.9 | 2.64294 | 3.65 |
| 34.5 | 2.59799 | 2.31 |
| 35.2 | 2.55115 | 2.01 |
| 35.6 | 2.51855 | 3.22 |
| 36.3 | 2.47209 | 1.77 |
| 36.8 | 2.44270 | 0.54 |
| 37.3 | 2.41347 | 2.40 |
| 37.7 | 2.38315 | 1.76 |
| 39.5 | 2.28084 | 0.13 |
| 40.1 | 2.24833 | 1.26 |
| 40.6 | 2.22413 | 0.93 |
| 41.9 | 2.15718 | 0.57 |
| 42.3 | 2.13551 | 0.66 |
| 42.8 | 2.11132 | 0.79 |
| 43.9 | 2.06411 | 0.76 |

[1]In this and all subsequent tables, the position 2θ is within ± 0.2.

In some embodiments, Form C of compound A is characterized in that it has one or more peaks in its X-ray powder diffraction pattern selected from those at about 7.0, about 16.1 and about 16.3 degrees 2-theta. In some embodiments, Form C of compound A is characterized in that it has two or more peaks in its X-ray powder diffraction pattern selected from those at about 7.0, about 16.1 and about 16.3 degrees 2-theta. In some embodiments, Form C of compound A is characterized in that it has all three peaks in its X-ray powder diffraction pattern selected from those at about 7.0, about 16.1 and about 16.3 degrees 2-theta.

Figure 7:
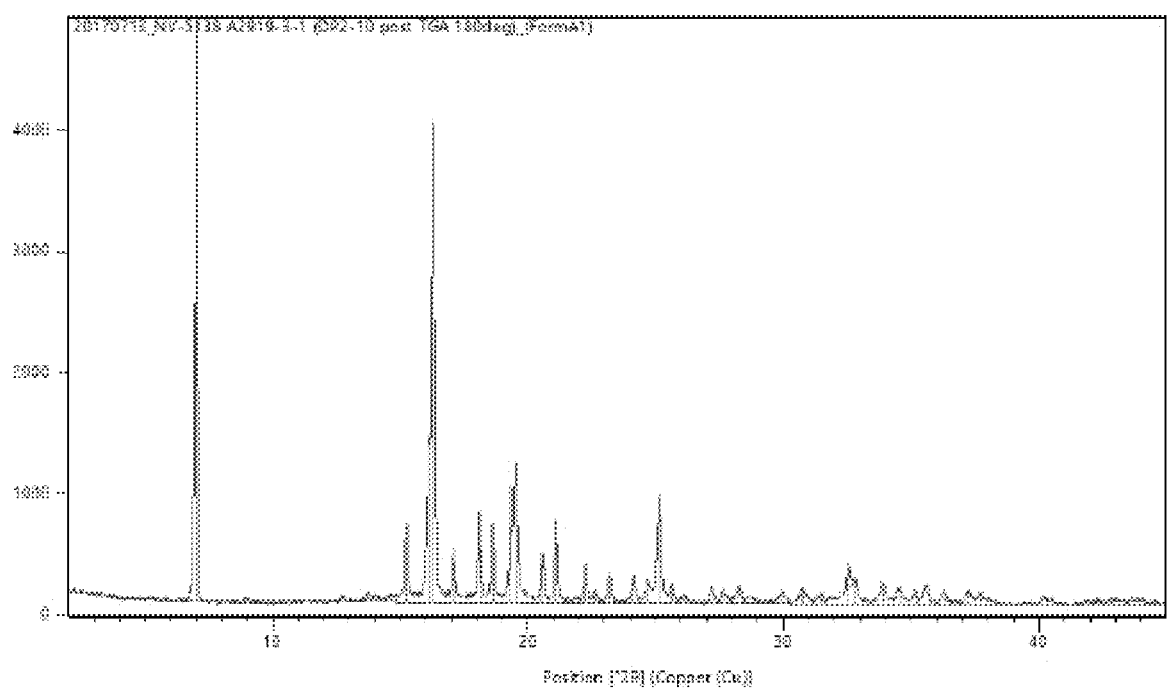
FIG. 7 depicts an XRPD pattern of Form C of compound A.

In certain embodiments, the X-ray powder diffraction pattern is substantially similar to the XRPD provided in FIG. 7.

Methods for preparing Form C of compound A are described infra.

In some embodiments, the present invention provides compound A:

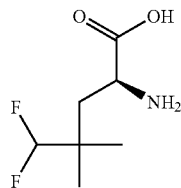

wherein said compound is crystalline.

In some embodiments, the present invention provides compound A, wherein said compound is substantially free of amorphous compound A.

In some embodiments, the present invention provides compound A, wherein said compound is substantially free of impurities.

In some embodiments, the present invention provides compound A, wherein said compound has one or more peaks in its XRPD selected from those at about 4.4, about 16.2 and about 17.7 degrees 2-theta. In some such embodiments, the present invention provides compound 1, wherein said compound has at least two peaks in its XRPD selected from those at about 4.4, about 16.2 and about 17.7 degrees 2-theta. In some such embodiments, the present invention provides Compound A, wherein said compound is of Form A.

In some embodiments, the present invention provides compound A, wherein said compound has an XRPD substantially similar to that depicted in FIG. 1.

In some embodiments, the present invention provides compound A, wherein said compound has one or more peaks in its XRPD selected from those at about 5.0, about 15.2 and about 17.5 degrees 2-theta. In some such embodiments, the present invention provides compound A, wherein said compound has at least two peaks in its XRPD selected from those at about 5.0, about 15.2 and about 17.5 degrees 2-theta. In some such embodiments, the present invention provides compound A, wherein said compound is of Form B.

In some embodiments, the present invention provides compound A, wherein said compound has an XRPD substantially similar to that depicted in FIG. 4.

In some embodiments, the present invention provides compound A, wherein said compound has one or more peaks in its XRPD selected from those at about 7.0, about 16.1 and about 16.3 degrees 2-theta. In some such embodiments, the present invention provides compound A, wherein said compound has at least two peaks in its XRPD selected from those at about 7.0, about 16.1 and about 16.3 degrees 2-theta. In some such embodiments, the present invention provides compound A, wherein said compound is of Form C.

In some embodiments, the present invention provides compound A, wherein said compound has an XRPD substantially similar to that depicted in FIG. 7.

In some embodiments, the present invention provides a composition comprising compound A and a pharmaceutically acceptable carrier or excipient.

In some embodiments, the present invention provides a compound selected from: compound A, Form A; compound A, Form B and compound A, Form C.

In some embodiments, the present invention provides a method of modulating mTORC1 activity in a patient comprising administering to said patient compound A or composition thereof. In some embodiments, the present invention provides a method of selectively modulating mTORC1 activity in a patient comprising administering to said patient compound A or composition thereof. In some embodiments, the present invention provides a method of activating mTORC1 in a patient comprising administering to said patient compound A or composition thereof.

In some embodiments, the present invention provides a method of treating a disease, disorder, or condition selected from treatment-resistant depression, a lysosomal storage disorder, JNCL, cystinosis, Fabry disease, MLIV, mental retardation or a genetic form of autism, comprising administering to a patient compound A or composition thereof.

In some embodiments, the present invention provides a method for preparing a solid form of compound A, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a solid form of compound A comprises one or more steps of heating or cooling a preparation.

In some embodiments, a method for preparing a solid form of compound A comprises one or more steps of agitating or stirring a preparation.

In some embodiments, a method for preparing a solid form of compound A comprises a step of adding a suitable acid to a solution or slurry of compound A.

In some embodiments, a method for preparing a solid form of compound A comprises a step of heating.

In certain embodiments, a solid form of compound A precipitates from the mixture. In another embodiment, a solid form of compound A crystallizes from the mixture. In other embodiments, a solid form of compound A crystallizes from solution following seeding of the solution (i.e., adding crystals of compound A to the solution).

A solid form of compound A can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a solid form of compound A is optionally isolated. It will be appreciated that a solid form of compound A may be isolated by any suitable physical means known to one of ordinary skill in the art. In certain embodiments, precipitated a solid form of compound A is separated from the supernatant by filtration. In other embodiments, precipitated solid form of compound A is separated from the supernatant by decanting the supernatant.

In certain embodiments, a solid form of compound A is separated from the supernatant by filtration.

In certain embodiments, an isolated solid form of compound A is dried in air. In other embodiments, isolated solid form of compound A is dried under reduced pressure, optionally at elevated temperature.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

Hydrate Forms of Compound A

In some embodiments, water and compound A are ionically bonded or hydrogen bonded to form compound 1, described below. It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary such solid forms of compound 1 is described in more detail below.

Compound 1 (Hydrate of Compound A)

According to one embodiment, the present invention provides a hydrate of compound A, represented by compound 1:

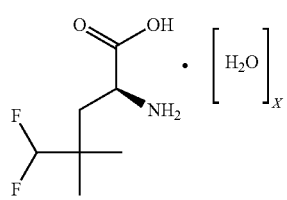

wherein 0<x≤about 1.

It will be appreciated by one of ordinary skill in the art that the water and compound A are ionically bonded or hydrogen bonded to form compound 1. It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary solid forms are described in more detail below.

In some embodiments, the present invention provides compound 1 substantially free of impurities. As used herein, the term "substantially free of impurities" means that the compound contains no significant amount of extraneous matter. Such extraneous matter may include excess 1,2-ethanedisulfonic acid, excess compound A, residual solvents, or any other impurities that may result from the preparation of, and/or isolation of, compound 1. In certain embodiments, at least about 95% by weight of compound 1 is present. In still other embodiments of the invention, at least about 99% by weight of compound 1 is present.

According to one embodiment, compound 1 is present in an amount of at least about 97, 97.5, 98.0, 98.5, 99, 99.5, 99.8 weight percent where the percentages are based on the total weight of the composition. According to another embodiment, compound 1 contains no more than about 3.0 area percent HPLC of total organic impurities and, in certain embodiments, no more than about 1.5 area percent HPLC total organic impurities relative to the total area of the HPLC chromatogram. In other embodiments, compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 1 is also meant to include all tautomeric forms of compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 1 can exist in a variety of solid forms. Exemplary such forms include polymorphs such as those described herein. In some embodiments, compound A and water are in about a 1:1 ratio. In some embodiments, water and compound A are in about a 1:2 ratio. In some embodiments, water and compound A are in about a 3:4 ratio. In some embodiments, water and compound A are in about a 1:4 ratio. In some embodiments, water and compound A are in about a 2:3 ratio. In some embodiments, water and compound A are in about a 1:3 ratio. In some embodiments, x is about ¼ for compound 1. In some embodiments, x is about ½ for compound 1. In some embodiments, x is about ¾ for compound 1. In some embodiments, x is about ⅔ for compound 1. In some embodiments, x is about ⅓ for compound 1. In some embodiments, x is about 1 for compound 1.

In certain embodiments, compound 1 is a crystalline solid. In other embodiments, compound 1 is a crystalline solid substantially free of amorphous compound 1. As used herein, the term "substantially free of amorphous compound 1" means that the compound contains no significant amount of amorphous compound 1. In certain embodiments, at least about 95% by weight of crystalline compound 1 is present. In still other embodiments of the invention, at least about 99% by weight of crystalline compound 1 is present.

It has been found that compound 1 can exist in at least one distinct polymorphic form. In some embodiments, the present invention provides a polymorphic form of Compound 1 referred to herein as Form A. In certain embodiments, Form A of compound 1 comprises about a 3:4 ratio of water and compound A. In certain embodiments, x is about ¾ for Form A of compound 1.

In some embodiments, compound 1 is amorphous. In some embodiments, compound 1 is amorphous, and is substantially free of crystalline compound 1.

Form A of Compound 1

In some embodiments, Form A of compound 1 has at least 1, 2, 3, 4 or 5 spectral peak(s) selected from the peaks listed in Table 4 below.

TABLE 4

XRPD Peak Positions for Form A of Compound 1

| Pos. [°2θ][1] | Rel. Int. [%] |
|---|---|
| 5.8 | 4.68662 |
| 8.4 | 8.38368 |
| 8.9 | 7.88716 |
| 10.2 | 22.3888 |
| 12.1 | 12.5225 |
| 15.2 | 5.87649 |
| 16.9 | 33.4848 |
| 17.1 | 100.00 |
| 17.3 | 69.1395 |
| 17.4 | 10.2511 |
| 17.6 | 51.5098 |
| 17.9 | 17.534 |
| 18.1 | 20.8017 |
| 18.3 | 92.648 |
| 19.0 | 5.66529 |
| 19.4 | 7.89022 |
| 20.6 | 18.3548 |
| 20.7 | 43.0262 |
| 20.8 | 4.93037 |
| 20.9 | 25.1766 |
| 22.2 | 13.6118 |
| 22.4 | 4.72072 |
| 23.4 | 28.7398 |
| 23.5 | 17.6636 |
| 24.5 | 10.0399 |
| 25.4 | 9.69082 |
| 25.5 | 4.9819 |
| 26.1 | 23.8361 |
| 26.7 | 5.4164 |
| 26.8 | 5.28821 |
| 26.9 | 5.25375 |
| 27.2 | 16.7917 |
| 28.0 | 5.88228 |
| 29.4 | 16.6576 |
| 30.4 | 16.3391 |
| 31.8 | 5.88242 |
| 32.8 | 11.489 |
| 33.6 | 11.3981 |
| 35.0 | 11.5181 |
| 35.1 | 7.77114 |
| 35.2 | 4.51035 |
| 35.7 | 5.72326 |
| 37.0 | 17.492 |
| 38.3 | 7.4528 |
| 38.8 | 4.79161 |
| 39.6 | 4.56053 |
| 40.6 | 6.02793 |

[1]In this and all subsequent tables, the position 2θ is within ± 0.2.

In some embodiments, Form A of compound 1 is characterized in that it has one or more peaks in its X-ray diffraction pattern selected from those at about 17.1, about 17.3 and about 18.3 degrees 2-theta. In some embodiments, Form A of compound 1 is characterized in that it has two or more peaks in its X-ray powder diffraction pattern selected from those at about 17.1, about 17.3 and about 18.3 degrees 2-theta. In some embodiments, Form A of compound 1 is characterized in that it has all three peaks in its X-ray powder diffraction pattern selected from those at about 17.1, about 17.3 and about 18.3 degrees 2-theta.

Figure 11:
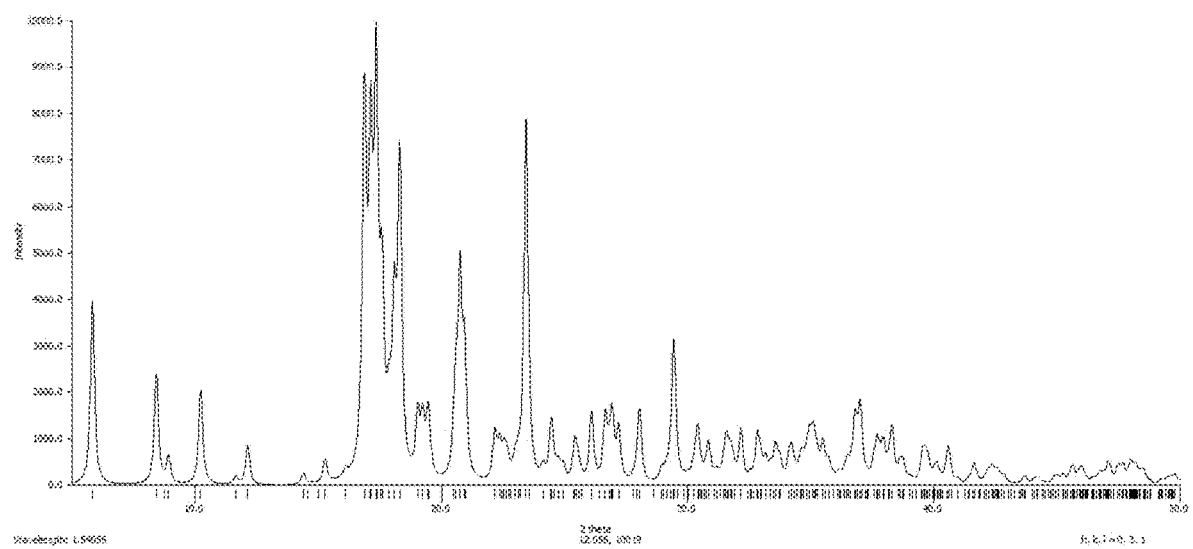
FIG. 11 depicts a simulated XRPD pattern of Form A of compound 1.

In certain embodiments, the X-ray powder diffraction pattern is substantially similar to the XRPD provided in FIG. 11. In certain embodiments, Form A of compound 1 comprises about 3:4 ratio of water and compound A. In certain embodiments, x is about ¾ for Form A of compound 1.

Methods for preparing Form A of compound 1 are described infra.

In some embodiments, the present invention provides compound 1:

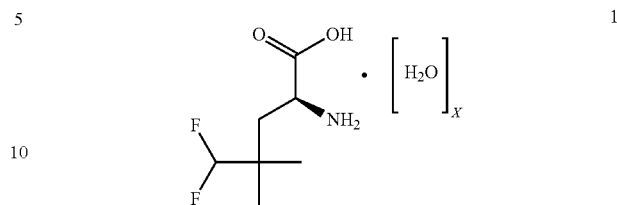

wherein 0<x≤about 1.

In some embodiments, the present invention provides compound 1, wherein said compound is crystalline.

In some embodiments, the present invention provides compound 1, wherein said compound is a crystalline solid substantially free of amorphous compound 1.

In some embodiments, the present invention provides compound 1, wherein said compound is substantially free of impurities.

In some embodiments, the present invention provides compound 1, wherein said compound has one or more peaks in its XRPD selected from those at about 17.1, about 17.3 and about 18.3 degrees 2-theta. In some such embodiments, the present invention provides compound 1, wherein said compound has at least two peaks in its XRPD selected from those at about 17.1, about 17.3 and about 18.3 degrees 2-theta. In some such embodiments, the present invention provides compound 1, wherein said compound is of Form A.

In some embodiments, the present invention provides compound 1, wherein said compound has an XRPD substantially similar to that depicted in FIG. 11.

In some embodiments, the present invention provides a composition comprising compound 1 and a pharmaceutically acceptable carrier or excipient.

In some embodiments, the present invention provides a compound selected from: compound 1, Form A.

In some embodiments, the present invention provides a method of modulating mTORC1 activity in a patient comprising administering to said patient compound 1 or composition thereof. In some embodiments, the present invention provides a method of selectively modulating mTORC1 activity in a patient comprising administering to said patient compound 1 or composition thereof. In some embodiments, the present invention provides a method of activating mTORC1 in a patient comprising administering to said patient compound 1 or composition thereof.

In some embodiments, the present invention provides a method of treating a disease, disorder, or condition selected from treatment-resistant depression, a lysosomal storage disorder, JNCL, cystinosis, Fabry disease, MLIV, mental retardation or a genetic form of autism, comprising administering to a patient compound 1 or composition thereof.

In some embodiments, the present invention provides a method for preparing a solid form of compound 1, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a solid form of compound 1 comprises one or more steps of heating or cooling a preparation.

In some embodiments, a method for preparing a solid form of compound 1 comprises one or more steps of agitating or stirring a preparation.

In some embodiments, a method for preparing a solid form of compound 1 comprises a step of adding a suitable acid to a solution or slurry of compound 1.

In some embodiments, a method for preparing a solid form of compound 1 comprises a step of heating.

In certain embodiments, a solid form of compound 1 precipitates from the mixture. In another embodiment, a solid form of compound 1 crystallizes from the mixture. In other embodiments, a solid form of compound 1 crystallizes from solution following seeding of the solution (i.e., adding crystals of compound 1 to the solution).

A solid form of compound 1 can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a solid form of compound 1 is optionally isolated. It will be appreciated that a solid form of compound 1 may be isolated by any suitable physical means known to one of ordinary skill in the art. In certain embodiments, precipitated a solid form of compound 1 is separated from the supernatant by filtration. In other embodiments, precipitated solid form of compound 1 is separated from the supernatant by decanting the supernatant.

In certain embodiments, a solid form of compound 1 is separated from the supernatant by filtration.

In certain embodiments, an isolated solid form of compound 1 is dried in air. In other embodiments, isolated solid form of compound 1 is dried under reduced pressure, optionally at elevated temperature.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably modulate mTORC1 activity, in a biological sample or in a patient. In certain embodiments, the amount of compound in compositions of this invention is such that is effective to measurably activate mTORC1, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulation of mTORC1 activity. In some embodiments, a provided compound, or composition thereof, is an activator of mTORC1.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the terms "mTORC1-mediated" disorders, diseases, and/or conditions as used herein means any disease or other deleterious condition in which mTORC1, is known to play a role. Accordingly, another embodiment of the present invention relates to treating or lessening the severity of one or more diseases in which mTORC1 is known to play a role.

In some embodiments, the method of activating mTORC is used to treat or prevent depression. (See Ignácio et al., (2015) Br J Clin Pharmacol. November 27). Accordingly, in some embodiments, the present invention provides a method of treating or preventing depression, in a patient in need thereof, comprising the step of administering to said patient a provided compound or pharmaceutically acceptable composition thereof. In some embodiments, the depression is treatment-resistant depression ("TRD"). In some embodiments, the treatment resistant depression is resistant to first line treatments. In some embodiments, the treatment resistant depression is resistant to second line treatments.

In some embodiments, the present invention provides a method of treating depression in a patient in need thereof, wherein said patient experiences a 50% reduction in depression scale score. In some embodiments, the patient experiences a 50% reduction in depression scale score within fewer than six weeks of administration of the compound or pharmaceutically acceptable composition. In some embodiments, the patient experiences a 50% reduction in depression scale score within fewer than four weeks of administration of the compound or pharmaceutically acceptable composition. In some embodiments, the patient experiences a 50% reduction in depression scale score within two weeks of administration of the compound or pharmaceutically acceptable composition. In some embodiments, the patient experiences a 50% reduction in depression scale score within fewer than two weeks of administration of the compound or pharmaceutically acceptable composition. In some embodiments, the patient experiences a 50% reduction in depression scale score within one week of administration of the compound or pharmaceutically acceptable composition. In some embodiments, the patient experiences a 50% reduction in depression scale score within seven days of administration of the compound or pharmaceutically acceptable composition. In some embodiments, the patient experiences a 50% reduction in depression scale score within six days of administration of the compound or pharmaceutically acceptable composition. In some embodiments, the patient experiences a 50% reduction in depression scale score within five days of administration of the compound or pharmaceutically acceptable composition. In some embodiments, the patient experiences a 50% reduction in depression scale score within four days of administration of the compound or pharmaceutically acceptable composition. In some embodiments, the patient experiences a 50% reduction in depression scale score within three days of administration of the compound or pharmaceutically acceptable composition. In some embodiments, the patient experiences a 50% reduction in depression scale score within two days of administration of the compound or pharmaceutically acceptable composition. In some embodiments, the patient experiences a 50% reduction in depression scale score within one day of administration of the compound or pharmaceutically acceptable composition. In some embodiments, the patient experiences a 50% reduction in depression scale score within twenty-four hours of administration of the compound or pharmaceutically acceptable composition. In some embodiments, the depression scale score is selected from the Montgomery-Asberg Depression Rating Scale (MADRS), the Hamilton Depression Rating Scale (HAMD-6), the Inventory of Depression Symptomatology Self-Rated Scale (IDS-SR), and the Clinical Global Impression Severity Scale (CGI-S).

In some embodiments, the present invention provides a method of treating depression in a patient in need thereof, comprising the step of orally administering to said patient a provided compound or pharmaceutically acceptable composition thereof, wherein the patient experiences a reduction in depression scale score comparable to ketamine administered via i.p. injection. In some embodiments, the reduction in depression scale score results from a single oral administration. In some embodiment, the reduction in depression scale score results from a plurality of oral administrations.

In some embodiments, the method of activating mTORC1 is used to elicit a rapid onset antidepressant activity. Accordingly, in some embodiments, the present invention provides a method of eliciting a rapid onset antidepressant activity, in a patient in need thereof suffering from TRD, comprising the step of administering to said patient a provided compound or pharmaceutically acceptable composition thereof. In some embodiments, the rapid onset antidepressant activity occurs within two weeks of administration of said compound or composition. In some embodiments, the rapid onset antidepressant activity occurs within one week of administration of said compound or composition. In some embodiments, the rapid onset antidepressant activity occurs within seven days of administration of said compound or composition. In some embodiments, the rapid onset antidepressant activity occurs within six days of administration of said compound or composition. In some embodiments, the rapid onset antidepressant activity occurs within five days of administration of said compound or composition. In some embodiments, the rapid onset antidepressant activity occurs within four days of administration of said compound or composition. In some embodiments, the rapid onset antidepressant activity occurs within three days of administration of said compound or composition. In some embodiments, the rapid onset antidepressant activity occurs within two days of administration of said compound or composition. In some embodiments, the rapid onset antidepressant activity occurs within one day of administration of said compound or composition. In some embodiments, the rapid onset antidepressant activity occurs within less than twenty-four hours of administration of said compound or composition.

In some embodiments, the present invention provides a method of eliciting a long-lasting, sustained antidepressant activity, in a patient in need thereof suffering from depression, comprising the step of administering to said patient a provided compound or pharmaceutically acceptable composition thereof. In some embodiments, the patient in need suffers from TRD. In some embodiments, the long-lasting, sustained antidepressant activity persists for at least twenty-four hours after a single administration of a provided compound or a pharmaceutically acceptable composition thereof. In some embodiments, the long-lasting, sustained antidepressant activity persists for longer than one day. In some embodiments, the long-lasting, sustained antidepressant activity persists for at least two days. In some embodiments, the long-lasting, sustained antidepressant activity persists for at least three days. In some embodiments, the long-lasting, sustained antidepressant activity persists for at least four days. In some embodiments, the long-lasting, sustained antidepressant activity persists for at least five days. In some embodiments, the long-lasting, sustained antidepressant activity persists for at least six days. In some embodiments, the long-lasting, sustained antidepressant activity persists for at least seven days.

In some embodiments, the present invention provides a method of eliciting antidepressant activity that is both rapid onset and long-lasting, sustained.

In some embodiments, the present invention provides a method of eliciting a positive behavioral response in a subject, comprising the step of administering to said subject a provided compound or pharmaceutically acceptable composition thereof. In some embodiments, the positive behavioral response correlates with an improvement in mood. In some embodiments, the positive behavioral response correlates with an reduction of anxiety. In some embodiments, the positive behavioral response corresponds with an improvement in mood. In some embodiments, the positive behavioral response correlates with an improved ability to cope with stress.

In some embodiments, the present invention provides a method of eliciting a rapid onset, positive behavioral response is a subject, comprising the step of administering to said subject a provided compound or pharmaceutically acceptable composition thereof. In some embodiments, the positive behavioral response occurs within twenty-four hours of administration. In some embodiments, the positive behavioral response occurs within one day of administration. In some embodiments, the positive behavioral response occurs within two days of administration. In some embodiments, the positive behavioral response occurs within three days of administration. In some embodiments, the positive behavioral response occurs within four days of administration. In some embodiments, the positive behavioral response occurs within five days of administration. In some embodiments, the positive behavioral response occurs within six days of administration. In some embodiments, the positive behavioral response occurs within seven days of administration. In some embodiments, the positive behavioral response occurs within one week of administration.

In some embodiments, the present invention provides a method of eliciting a long-lasting, sustained positive behavioral response in a subject, comprising the step of administering to said patient a provided compound or pharmaceutically acceptable composition thereof. In some embodiments, the long-lasting, sustained positive behavioral response persists for longer than one day. In some embodiments, the long-lasting, sustained positive behavioral response persists for at least two days. In some embodiments, the long-lasting, sustained positive behavioral response persists for at least three days. In some embodiments, the long-lasting, sustained positive behavioral response persists for at least four days. In some embodiments, the long-lasting, sustained positive behavioral response persists for at least five days. In some embodiments, the long-lasting, sustained positive behavioral response persists for at least six days. In some embodiments, the long-lasting, sustained positive behavioral response persists for at least seven days.

In some embodiments, the present invention provides a method of eliciting a positive behavioral response that is both rapid onset and long-lasting, sustained.

In some embodiments, the present invention provides a method of ameliorating and/or reversing behavioral and synaptic defects caused by chronic, unpredictable stress (CUS), in a patient in need thereof, comprising the step of administering to said patient a provided compound or pharmaceutically acceptable composition thereof. In some embodiments, the method ameliorates and/or reverses behavioral defects caused by CUS. In some embodiments, the method ameliorates and/or reverses synaptic defects caused by CUS. In some embodiments, the synaptic defect caused by CUS is a decrease in postsynaptic protein expression. In some embodiments, the decrease in postsynaptic protein expression is a decrease in the expression of GLUR1 or PSD95.

In some embodiments, the method of activating mTORC1 is used to treat or prevent forms of autism. (See Novarino et al., (2012) Science 19 October, 338:6105, pp. 394-397). Accordingly, in some embodiments, the present invention provides a method of treating or preventing a form of autism, in a subject in need thereof, comprising the step of administering to said subject a provided compound or pharmaceutically acceptable composition thereof. In some embodiments, the autism is a genetic form of autism.

In some embodiments, the present invention provides a method of treating a genetic form of autism in a patient in need thereof, comprising the step of administering to said patient a provided compound or pharmaceutically acceptable composition thereof. SHANK3 haploinsufficiency is causative for the neurological features of Phelan-McDermid syndrome (PMDS), including a high risk of autism spectrum disorder (Bidinosti et al. (2016) Science Reports 351, 1199-1203). Down regulation of mTORC1 in SHANK3 deficient neurons is due to enhanced phosphorylation and activation of serine/threonine protein phosphatase 2A (PP2A) regulatory subunit, B56b, by its kinase, Cdc2-like kinase 2 (Bidinosti et al. (2016) Science Reports 351, 1199-1203). SHANK3 mutant mice show autistic traits (Yang et al. (2012) The Journal of Neuroscience 32, 6525-6541). Patients with autistic traits and motor delays carry deleterious homozygous mutations in the SLC7A5 gene. Solute carrier transporter 7a5 (SLC7A5), a large neutral amino acid transporter localized at the blood brain barrier (BBB), has an essential role in maintaining normal levels of brain BCAAs. Leucine intracerebroventricular administration ameliorates abnormal behaviors in adult mutant mice (Tarlungeanu et al. (2016) Cell 167, 1481-1494).

In some embodiments, the present invention provides a method of treating a Lysosomal Storage Disease or Disorder ("LSD") in a patient in need thereof, comprising the step of administering to said patient a provided compound or pharmaceutically acceptable composition thereof. LSDs are a group of inherited metabolic disorders that result from defects in lysosomal function. Lysosomal storage disorders are caused by lysosomal dysfunction usually as a consequence of deficiency of a single enzyme required for the metabolism of lipids, glycoproteins (sugar containing proteins) or so-called mucopolysaccharides. In some embodiments, the present invention provides a method of treating a lipid storage disorder in a patient in need thereof, comprising the step of administering to said patient a provided compound or pharmaceutically acceptable composition thereof. In some embodiments, the lipid storage disorder is selected from a sphingolipidose (e.g., gangliosidosis, Gaucher, Niemann-Pick disease, or Metachromatic leukodystrophy). In some embodiments, the present invention provides a method of treating a gangliosidosis (e.g., Tay-Sachs disease or a leukodystrophy). In some embodiment, the present invention provides a method of treating a mucopolysaccharidoses in a patient in need thereof, comprising the step of administering to said patient a provided compound or pharmaceutically acceptable composition thereof. In some embodiments, the mucopolysaccharidoses is Hunter syndrome or Hurler disease.

In some embodiments, the present invention provides a method of treating JNCL (Batten Disease) in a patient in need thereof, comprising the step of administering to said patient a provided compound or pharmaceutically acceptable composition thereof. JNCL is caused by the deletion of exons 7 and 8 of the CLN3 gene resulting in a nonfunctional protein. Battenin, the full-length protein encoded by CLN3, is a transmembrane protein that localizes to the late endosome and lysosome where it has been shown to help regulate pH, amino acid balance and vesicle trafficking (Pearce et al. (1999) Nature Genetics 22, 1; Fossale et al. (2004) BMC Neuroscience 10, 5) mTOR activation requires intracellular nutrients provided by autophagy which, in in vitro and in vivo models of JNCL, are lowered due to the lack of functional battenin (Cao et al. (2006) Journal of Biological Chemistry 281, 29).

In some embodiments, the present invention provides a method of treating cystinosis in a patient in need thereof, comprising the step of administering to said patient a provided compound or pharmaceutically acceptable composition thereof. Cystinosis is an autosomal recessive disease affecting those with two alleles mutated in the CSTN gene; the lysosomal cystine transporter cystinosin is defective in efflux of cystine from the lysosome, resulting in cystine crystal formation in renal epithelial tubules and loss of kidney function. Studies have shown defective or reduced mTORC1 signalling in cells lacking CSTN and mislocalized mTOR (Ivanova et al. (2016) J Inherit Metab Dis. 39(3), 457-64; Andrzejewska et al. (2016) J Am Soc Nephrol. 27(6), 1678-1688e). These defects could not be rescued by cysteamine (Ivanova et al. (2016) J Inherit Metab Dis. 39(3), 457-64; Andrzejewska et al. (2016) J Am Soc Nephrol. 27(6), 1678-1688e). Cystinosin has also been found to bind mTORC1 pathway components v-ATPase, Rags, and Ragulator (Andrzej ewska et al. (2016) J Am Soc Nephrol. 27(6), 1678-1688e). CTNS-deficient cells show and increased number of autophagosomes and reduced chaperone-mediated autophagy (Napolitano et al. (2015) EMBO Mol Med. 7(2), 158-74).

In some embodiments, the present invention provides a method of treating Fabry disease in a patient in need thereof, comprising the step of administering to said patient a provided compound or pharmaceutically acceptable composition thereof. In Fabry disease, deficiencies in alpha-galactosidase results in the lysosomal accumulation of globotriaosylceramide lipids. Decreased mTOR activity and increased autophagy is observed in vitro and in vivo in a cell model of Fabry in which alpha-galactosidase is knocked down with shRNA (Liebau et al. (2013) PLoS 8, e63506). Hyperactive autophagy is also observed in the brains of mice in which alpha-galactosidase is knocked out (Nelson et al. (2014) Acta Neuropathologica Communications 2, 20).

In some embodiments, the present invention provides a method of treating Mucolipidosis type IV (MLIV) in a patient in need thereof, comprising the step of administering to said patient a provided compound or pharmaceutically acceptable composition thereof. In MLIV, mutations of theTRPML1 lysosomal Ca(2+) channel cause disordered lysosomal membrane trafficking. An MLIV knockout in *Drosophila* resulted in upregulation of autophagy and a decrease in mTOR activity, both of which could be reversed by activating mTORC1 genetically or by feeding animals a high protein diet (Wong et al. (2012) Curr Biol. 22(17), 1616-1621). Increased autophagy is also observed in fibroblasts from MLIV patients (Vergarajauregui et al. (2008) Human Molecular Genetics 17, 2723-2737).

In some embodiments, the present invention provides a method of treating mental retardation in a patient in need thereof, comprising the step of administering to said patient a provided compound or pharmaceutically acceptable composition thereof. In *Homo sapiens*, Cereblon mutations are linked to a mild form of autosomal recessive non-syndromic mental retardation. In a mouse cereblon knockout model of retardation, loss of cereblon activates AMPK, inhibits mTOR and reduces protein translation in the cerebellum (Lee et al. (2014) J Biol Chem. 289, 23343-52; Xu et al. (2013) J Biol Chem. 288, 29573-85).

In some embodiments, the present invention provides a method of increasing neuronal protein expression in a subject, comprising the step of administering to said subject a provided compound or pharmaceutically acceptable composition thereof. In some embodiments the increase in neuronal protein expression occurs in a post-synaptic neuron. In some embodiments, the increase in neuronal protein expression includes increased expression of brain-derived neurotrophic factor (BDNF). In some embodiments, the increase in neuronal protein expression includes increased expression of glutamate receptor 1 (GluR1). In some embodiments, the increase in neuronal protein expression includes increased expression of synapsin. In some embodiments, the increase in neuronal protein expression includes increased expression ofPSD95.

In some embodiments, the present invention provides a method of increasing synaptogenesis in a subject, comprising the step of administering to said subject a provided compound or pharmaceutically acceptable composition thereof. In some embodiments the increased synaptogenesis involves synaptic remodelling. In some embodiments, the increased synaptogenesis involves induction of dendritic spines. In some embodiments, the induction of dendritic spines causes an increased density of dendritic spines. In some embodiments, the dendritic spines are thin spines. In some embodiments, the dendritic spines are mushroom spines.

In some embodiments, the present invention provides a method of enhancing synoptic function in a subject, comprising the step of administering to said subject a provided compound or pharmaceutically acceptable composition thereof. In some embodiments, the enhanced synoptic function in a subject involves an increase in excitatory postsynaptic currents (EPSC).

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating, or selectively modulating, mTORC1 activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of activating mTORC1 in a patient comprising the step of administering to said patient a compound of the present invention, or a composition comprising said compound.

According to another embodiment, the present invention provides a method for treating a disorder mediated by mTORC1 in a patient in need thereof, comprising the step of administering to said patient a compound according to the present invention or pharmaceutically acceptable composition thereof. Such disorders are described in detail herein.

Combinations with Other Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, a provided compound is administered in combination with an antidepressant therapeutic agent. Antidepressant therapeutic agents are well known to one of ordinary skill in the art and include Selective Serotonin Reuptake Inhibitors ("SSRI", e.g. sertraline, escitalopram, citalopram, fluvoxamine, fluoxetine, paroxetine), anti-depressant (e.g., bupropion, venlafaxine, mirtazapine, duloxetine, amitriptyline, imipramine, selegiline, nortriptyline, trazodone, desvenlafaxine, and aripiprazole).

In some embodiments, a provided compound is administered in combination with an additional therapeutic agent or process useful for treating one or more LSDs. In some embodiments, a provided compound is administered in combination with enzyme replacement therapy, chemical chaperone therapy, bone marrow transplantation, substrate reduction therapy, α-L-iduronidase, Recombinant human N-acetylgalactosamine-4-sulphatase (arylsulphatase B), an inhibitor of glycosphingolipid biosynthesis, N-butyldeoxynojirimycin (Miglustat), a hydrophobic iminosugar, or an inhibitor of α-galactosidase A (e.g., 1-deoxy-galactonojirimycin).

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

X-ray powder diffraction (XRPD) analysis was carried out in transmission mode on a Panalytical X'Pert Pro or Empyrean instrument with X'Celerator detector using a standard Aptuit method. The data were evaluated using the HighScore Plus software. The instrumental parameters used are listed below in Table 5.

TABLE 5

Parameters used for X-ray powder diffraction (XRPD) analysis.

| Instrumental Parameter | Value |
|---|---|
| °2θ range | 2-45 |
| Step size [°2θ] | 0.0170 |
| Time per step [sec] | 60.7285 sec |
| Wavelength [nm] | 0.154060 (Cu K-Alpha1) |
| Rotation [Yes/No] | Yes |
| Slits divergence/Antiscatter. | Incident Mask fixed 10 mm; Divergence slits ½°, Antiscatter slit ½° on incident beam; 1/32° on diffracted |
| X-ray Mirror | Inc. Beam Cu W/Si focusing MPD, Acceptance Angle 0.8°, Length 55.3 mm |
| Temperature | Room temperature |
| Humidity values [% RH] | Ambient |
| Fixed Slits | 0.02 rad fixed Soller slits on incident and diffracted beam |
| Monochromator | None |
| Detector type | X'Celerator (active length 2.122 2θ°), scanning mode |
| Sample holder | Transmission sample holder. Use Insert to keep thickness at 1 mm, 5 mm diameter |
| Configuration | Transmission |
| Generator voltage/current | 40 KV/40 mA |

The XRPD analysis at controlled environmental conditions were collected in reflection mode on a Panalytical Empyrean instrument equipped with a Anton-Paar CHC+ chamber with Pixel3D detector. The data were evaluated using the HighScore Plus software. The instrumental parameters used are listed below in Table 6.

TABLE 6

Parameters used for X-ray powder diffraction (XRPD) analysis at controlled conditions.

| Instrumental Parameter | Value |
|---|---|
| °2θ range | 3-20 |
| Step size [°2θ] | 0.013 |
| Time per step [sec] | ~180 |
| Wavelength [nm] | 0.15406 (Cu K-Alpha1) |
| Rotation [Yes/No] | No |
| Slits divergence/antiscatter. | Fixed Divergence slits 1/32°, Antiscatter slits fixed 1/8° |
| X-ray Mirror | Bragg Brentano HD |
| Temperature | 25° C. |
| Humidity values [% RH] | FOR BATCH A/2919/13/1:<br>$1^{st}$ adsorption cycle: 50, 60, 70, 80, 90% RH<br>$1^{st}$ desorption cycle: 80, 70, 60, 50, 40, 30, 20, 10% RH<br>$2^{nd}$ adsorption cycle: 20, 30, 40, 50% RH<br>$2^{nd}$ desorption cycle: 5% RH<br>$3^{rd}$ adsorption cycle: 90% RH<br>$3^{rd}$ desorption cycle: 50, 5% RH<br>$4^{th}$ adsorption cycle: 50% RH<br>FOR BATCH A2944-14-1 at 180° on CHC New Snip:<br>$1^{st}$ adsorption cycle: 50, 70, 90% RH<br>$1^{st}$ desorption cycle: 50, 30, 10, 5% RH<br>$2^{nd}$ adsorption cycle: 30, 50, 70, 90% RH |
| Fixed Slits | 0.02 rad fixed Soller slits on incident and diffracted beam |
| Monochromator | None |
| Detector type | PIXcel3D-Medipix3 1 × 1 |
| Sample holder | Zero Background sample holder for CHC + chamber |
| Configuration | Reflection |
| Generator voltage/current | 45 KV/40 mA |

Thermogravimetric Analysis (TGA) was carried out using a TA Q5000IR instrument. The method parameters are listed below in Table 7.

TABLE 7

Parameters used for thermogravimetric analysis.

| Instrumental Parameter | Value |
|---|---|
| Balance purge gas [mL/min] | 10 |
| Sample purge gas [mL/min] | 25 |
| Gas | Nitrogen |
| Temperature-Time-Rate | Typically from room temperature to 350° C. at 10° C./min |
| Typical sample amount [mg] | Usually from 2 mg to 20 mg |
| Pan [Pt/Al] | Sealed Aluminum (punched) |

Differential Scanning Calorimetry (DSC) analyses were carried out using a TA Q2000 MDSC instrument. The method parameters are listed below in Table 8.

TABLE 8

Parameters used for differential scanning calorimetry analysis.

| Instrumental Parameter | Value |
|---|---|
| Cooling [ON/OFF] | ON |
| Gas | Nitrogen |
| Temperature-Time-Rate | From 0° C. to ~280° C. Ramp at 10° C./min. |

TABLE 8-continued

Parameters used for differential scanning calorimetry analysis.

| Instrumental Parameter | Value |
|---|---|
| Typical sample amount [mg] | Usually from 0.5 mg to 2.5 mg |
| Pan | Aluminum |

Chiral HPLC analysis was carried out with the parameters listed below in Table 9.

TABLE 9

Parameters used for chiral HPLC analysis.

| Instrumental Parameter | Value |
|---|---|
| Column type | Chiralpak ZWIX (+) (25 × 0.4 cm) 3 um |
| Mobile phase | Methanol/Acetonitrile/Water (42/56/2% v/v) + 0.1% isopropylamine + 0.1% formic acid |
| Flow rate [mL/min] | 0.8 |
| DAD | — |
| ELSD | P = 3.5 bar; T = 40 C. |
| Loop | 10 μL |
| Enantiomer 1 retention time | 11.1 min |
| Enantiomer 2 retention time | 13.1 min |

Gravimetric Vapour Sorption (GVS) analyses were carried out on an IGASorp instrument by Hiden Analytical. The method parameters are listed below in Table 10.

TABLE 10

Parameters used for gravimetric vapour sorption analysis.

| Instrumental Parameter | Value |
|---|---|
| Temperature (° C.) | 25 |
| Temperature stability (° C./min) | 0.2 |
| Flow Rate (mL/min) | 500 |
| Min Time (min) | 10 |
| Timeout (min) | 120 |
| Scans | 3 |
| Initial conditions | 50% RH, 25° C., starting with absorption |
| Humidity values (% RH) | 1st Adsorption curve: 50-90<br>1st Desorption curve: 90-0<br>2nd Absorption curve: 0-90<br>with 10% RH step |

Compound A may be prepared according to the methods described in U.S. Pat. No. 10,100,066, the entirety of which is incorporated herein by reference.

Example 1—Preparation of Free Base Form A of Compound A

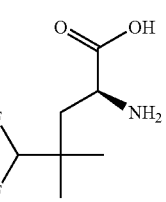

A

Form A of Compound A

Form A of compound A was prepared as described below.

Form A of Compound A—Preparation Method 1

A slurry was set up by weighing about 65 mg of compound A and suspending compound A in 0.8 mL of acetone and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form A of Compound A—Preparation Method 2

A slurry was set up by weighing about 55 mg of compound A and suspending compound A in 1.0 mL of acetonitrile and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form A of Compound A—Preparation Method 3

A slurry was set up by weighing about 60 mg of compound A and suspending compound A in 0.8 mL of 1-butanol and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form A of Compound A—Preparation Method 4

A slurry was set up by weighing about 60 mg of compound A and suspending compound A in 0.5 mL of 2-butanone (MEK) and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form A of Compound A—Preparation Method 5

A slurry was set up by weighing about 55 mg of compound A and suspending compound A in 0.7 mL of ethyl acetate and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form A of Compound A—Preparation Method 6

A slurry was set up by weighing about 55 mg of compound A and suspending compound A in 0.9 mL of isopropanol and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Table 1, supra, is reproduced below and sets forth the X-ray diffraction peaks observed for Form A of compound A.

TABLE 1

XRPD Peak Positions for Form A of Compound A.

| Pos. [°2θ] | d-spacing [Å] | Rel. Int. [%] |
|---|---|---|
| 4.4 | 19.96942 | 100.00 |
| 6.1 | 14.45004 | 25.45 |
| 6.2 | 14.21554 | 22.07 |
| 8.7 | 10.20120 | 11.00 |
| 8.8 | 10.00741 | 10.76 |
| 12.2 | 7.23011 | 9.66 |
| 14.4 | 6.16658 | 6.34 |
| 15.6 | 5.66238 | 26.43 |
| 16.2 | 5.45686 | 81.29 |
| 16.7 | 5.31669 | 7.92 |
| 17.3 | 5.11234 | 68.23 |
| 17.5 | 5.07462 | 64.89 |
| 17.7 | 5.00663 | 88.87 |
| 18.4 | 4.82874 | 5.82 |
| 19.4 | 4.56431 | 23.79 |
| 19.6 | 4.52142 | 30.99 |
| 20.1 | 4.42642 | 5.20 |
| 20.3 | 4.37616 | 15.93 |
| 20.8 | 4.27126 | 21.94 |
| 21.1 | 4.21293 | 12.75 |
| 22.2 | 4.00638 | 14.90 |
| 22.5 | 3.95102 | 4.50 |
| 23.1 | 3.84773 | 8.84 |
| 23.6 | 3.76897 | 23.73 |
| 25.0 | 3.56717 | 9.90 |
| 25.3 | 3.52477 | 17.35 |
| 26.2 | 3.39632 | 17.70 |
| 26.7 | 3.33700 | 8.63 |
| 26.9 | 3.31631 | 5.15 |
| 28.1 | 3.17794 | 3.60 |
| 28.9 | 3.08581 | 2.40 |
| 29.6 | 3.01622 | 4.77 |
| 30.3 | 2.95375 | 5.72 |
| 30.6 | 2.92314 | 5.39 |
| 30.9 | 2.89490 | 12.46 |
| 31.0 | 2.88869 | 14.44 |
| 31.6 | 2.83502 | 29.78 |
| 32.8 | 2.73158 | 17.12 |
| 33.8 | 2.65090 | 9.60 |
| 34.7 | 2.58456 | 3.04 |
| 35.1 | 2.55777 | 5.93 |
| 36.1 | 2.49100 | 4.11 |
| 37.1 | 2.42595 | 6.69 |
| 38.3 | 2.34795 | 4.11 |
| 38.7 | 2.32505 | 8.85 |
| 39.8 | 2.26429 | 3.32 |
| 40.9 | 2.20715 | 3.73 |
| 41.8 | 2.15870 | 1.37 |
| 42.9 | 2.10893 | 1.92 |
| 43.6 | 2.07629 | 0.89 |

FIG. 1 depicts an XRPD pattern of Form A of compound A.

Figure 2:
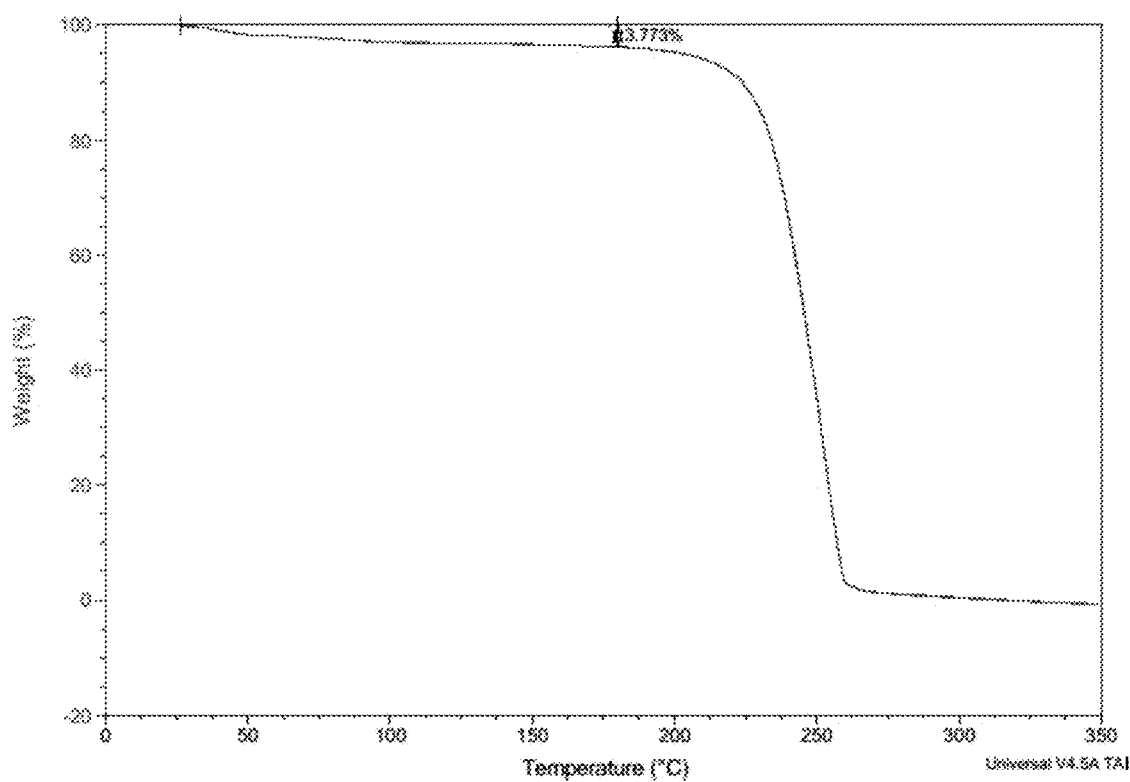
FIG. 2 depicts a TGA trace of Form A of compound A.

FIG. 2 depicts a DSC trace of Form A of compound A.

Figure 3:
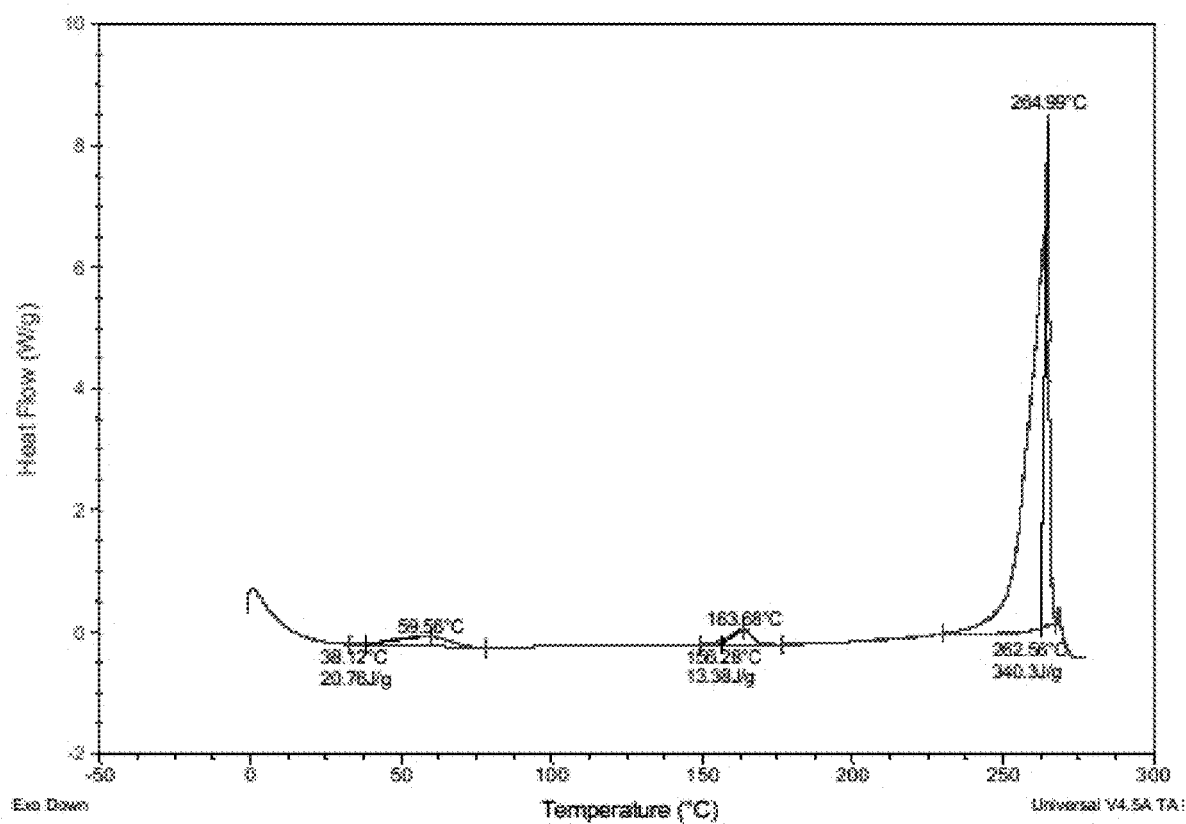
FIG. 3 depicts a DSC trace of Form A of compound A.

FIG. 3 depicts a TGA trace of Form A of compound A.

Example 2—Preparation of Free Base Form B of Compound A

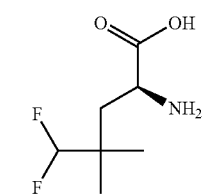

A

Form B of Compound A

Form B of compound A was prepared as described below.

Form B of Compound A—Preparation Method 1

About 4 g of compound A was suspended in IPA/water 70:30, 5 vol (20 mL; overall volume 24 mL, 167 mg/mL) in a 50 mL EasyMax reactor equipped with FBRM Lasentec® probe to monitor the crystallization progression. The content was heated to the maximum temperature allowed by the system (79° C.). Stirring with propeller blades was applied. The compound tended to dissolve slowly. As dissolution was not achieved, 1 vol of solvent mixture was added. A clear solution with some heavy plate particles and encrustation in the upper space of the reactor was observed. Additional 0.5 vol of solvent mixture were added; particles disappeared but some crusts remained (total volume 30 mL, 133 mg/mL). The content was cooled to 76° C. at 0.5 K/min. After few minutes, seed (30 mg, 1% w/w calculated on the expected output) was added as freshly prepared suspensions in IPA/water 70/30 (0.2 mL) but it was instantaneously dissolved. The content was cooled to 72° C. at 0.5 K/min. After few minutes, dry seed (30 mg, 1% w/w calculated on the expected output) was added again. The content was held at this temperature for 4 hours to verify the seed persistence and then cooled to 20° C. at 0.2 K/min. The material, initially crystallized, appeared completely dissolved within 1 hour and self-crystallized at 50° C. during the cooling ramp. At 20° C. significant encrustations along the wall above the solvent as well as on the bottom of the reactor were observed. With a spatula, crusts were pushed into the slurry and after some time the slurry became homogeneous. A sampling was collected for XRPD analysis, which yielded Form B.

Due to the high volumes involved, the experiment was continued in a 100 mL reactor. The reactor was quickly heated to internal 80° C. About 1 mL of solvent was required to compensate its evaporation. The solution appeared clear but a ring of crust was persistent. The content was cooled to 74° C. at 0.5 K/min. After few minutes, dry seed (A/2919/27/3—30 mg, 1% w/w calculated on the expected output) was added. The seed did not dissolve within 1 hour. IPA (13 vol, 52 mL) was added with a rate of 0.3 mL/min (3 hours). During this time, the content was held at 74° C. IPA addition caused massive precipitation generating jelly-like slurry that the impeller was not able to stir. The content was cooled to 20° C. at 0.2 K/min. A static solid mass was found the day after with stirring limited to the central part of the impeller. By moving the solid mass with a spatula the slurry became mobile and homogeneous. The solid was isolated by filtration on filter syringe (PTFE frit, porosity 20 μm). During this operation, some mother liquors recycling were required to fully recover the material from the reactor. A sample was collected for XRPD analysis after de-liquoring before wash, which yielded Form B plus some extra reflections. Wash (IPA/water 90/10, 10 mL, about 1 cake volume) was then applied and the solid was dried under vacuum for 1 hour. A sample was collected for XRPD analysis after washing, which yielded Form B. The solid was dried in vacuum oven at 40° C. for 20 hours.

Form B of Compound A—Preparation Method 2

About 4 g of compound A was suspended in IPA/water 70:30, 5 vol (20 mL; overall volume 24 mL, 167 mg/mL) in a 50 mL EasyMax reactor equipped with FBRM Lasentec® probe to monitor the crystallization progression. Stirring with propeller blades was applied at 500 rpm. The content was heated to the maximum temperature allowed by the system (81° C., rate: 3K/min) but full dissolution was not achieved (Lasentec: 1800 counts) therefore 1 vol of solvent mixture was added. Crusts formation on the reactor walls above the solvent level was observed. Temperature was lowered to 78° C. to remain below the boiling point of the solvent mixture and additional 0.5 vol of solvent were added; suspended particles disappeared but some crusts remained (total volume 30 mL, 133 mg/mL). The content was cooled to 75° C. with a 0.5 K/min rate. After few minutes, dry seed (A/2919/27/3—30 mg, 1% w/w calculated on the expected output) was added. Lasentec counts jumped to 33000 and then began to decrease rapidly. Temperature was lowered to 73° C. (rate 0.5 K/min) to prevent complete dissolution (as observed in the previous experiment A/2919/40) and a sampling was performed for a check of the crystal form: A/2919/42/1 (wet) showed presence of Form2 in mixture with unassigned reflections by XRD analysis. The reactor was held at 73° C. for 4 hours and then cooled to 20° C. at 0.2 K/min. While the reactor was kept at 73° C., Lasentec counts continued to decrease slowly before the cooling ramp started: this may be due to crusts formation phenomenon. At 20° C. the content appeared with huge encrustations along the reactor wall above the solvent level. With spatula crusts were pushed into the slurry. A sample was collected for XRPD analysis, which yielded Form B.

In order to better clarify what happens after seeding, the material was re-dissolved at 79° C. (3K/min). A few crusts were present on the reactor walls. Temperature was lowered at 70° C. with a 0.2 k/min rate. The solution remained clear but presence of crusts on the wall increased. After 90 mins dry seed (A/2919/27/3—30 mg, 1% w/w calculated on the expected output) was added. Lasentec counts jumped to 35000 and then began to decrease. After 1 hr a sample was collected and submitted to XRPD analysis, which yielded Form B. After 2 hrs from the seed addition, Lasentec counts were decreased to 15000 and large crusts were present on the reactor wall. With spatula crusts were pushed into the slurry and the Lasentec counts rose to 29000. These evidences confirm that crusts formation on the reactor wall lead to a decrease of the product concentration in the system, which can contribute in making the seeding procedure difficult to control (and also functioning as self-seeding).

Due to the high volumes involved, the experiment was continued in a 100 mL reactor. The reactor was quickly heated to internal 80° C. This time, stirring with anchors was applied at 200 rpm. About 1 mL of solvent was required to compensate the evaporation. The solution appeared clear but a ring of crust was present. The jacket was cooled to 75° C. at 0.5 K/min and after few minutes, the material self-crystallized. The content was heated again at 80° C. until complete dissolution was reached. After about 10 minutes, temperature was lowered to ~74° C. [Tjacket=81.5° C.] and dry seed (A/2919/27/3—30 mg, 1% w/w calculated on the expected output) was added. The seed did not dissolve within 20 mins. IPA (13 vol, 52 mL) was added at rate of 0.3 mL/min (3 hours). During this time, the jacket was held at 81.5° C. IPA caused massive precipitation generating jelly-like slurry. The content was cooled to 20° C. at 0.2 K/min. A mobile and homogeneous mass was found the day after, a few crusts were observed on the reactor wall. The solid was isolated by filtration on filter funnel (DURAN®, porosity 3). Some mother liquors recycling were required to fully recover the product from reactor. A sample was collected for XRPD analysis after deliquoring and before wash, which yielded Form B. Wash (IPA/water 90/10, 10 mL, about 1 cake volume) was applied. Solid dried in vacuum oven at 40° C. for 6 hours.

Form B of Compound A—Preparation Method 3

About 6 g of compound A was suspended in IPA/water 70:30, 6.5 vol (39 mL; overall volume 45 mL, 133 mg/mL) in a 100 mL EasyMax reactor equipped with anchor. The content was heated to 78° C. A clear solution was obtained. A ring of crust was present above the liquid level. The content was cooled to 74° C. at 0.5 K/min. After few minutes, dry seed (A/2919/27/3—30 mg, 0.6% w/w calculated on the expected output) was added. The seed was persistent. IPA (13 vol, 78 mL) was added at rate of 0.44 mL/min (3 hours). During this time, the content was held at 74° C. After the addition, the content was cooled to 20° C. at 0.2 K/min. The solid was then isolated by filtration on gooch (porosity 3), some mother liquors recycling was required to fully recover the material from reactor. Wash (IPA/water 90/10, 12 mL, 2 vol) was applied. A sample was collected for XRPD analysis after wash, which yielded Form B. The solid was dried under vacuum for 1 hour and then in vacuum oven at 40° C. for 5 hours.

Form B of Compound A—Preparation Method 4

A slurry was set up by weighing about 65 mg of compound A and suspending compound A in 0.5 mL of methyl isobutyl ketone (MIBK) and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form B of Compound A—Preparation Method 5

A slurry was set up by weighing about 55 mg of compound A and suspending compound A in 0.6 mL of methyl t-butyl ether (MTBE) and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form B of Compound A—Preparation Method 6

A slurry was set up by weighing about 60 mg of compound A and suspending compound A in 0.8 mL of toluene and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form B of Compound A—Preparation Method 7

A slurry was set up by weighing about 70 mg of compound A and suspending compound A in 0.7 mL of isopropanol/water (90:10) and visually checking that excess solid remained un-dissolved (magnetic stirring at ca. 500-700 rpm was applied). The slurry was stirred at 20° C. for 14 days. Solids were isolated by filtration and dried in vacuum for ~2 hrs at room temperature.

Form B of Compound A—Preparation Method 8

A slurry was set up by weighing about 60 mg of compound A and suspending compound A in 0.8 mL of acetone/water (90:10) and visually checking that excess solid remained un-dissolved (magnetic stirring at ca. 500-700 rpm was applied). The slurry was temperature cycled between 20° C. and 40° C. in 2 hour cycles for a total of 6 cycles overnight. Solids were isolated by filtration and dried in vacuum for ~1-2 hrs at room temperature.

Form B of Compound A—Preparation Method 9

A slurry was set up by weighing about 70 mg of compound A and suspending compound A in 0.7 mL of isopropanol/water (90:10) and visually checking that excess solid remained un-dissolved (magnetic stirring at ca. 500-700 rpm was applied). The slurry was temperature cycled between 20° C. and 40° C. in 2 hour cycles for a total of 6 cycles overnight. Solids were isolated by filtration and dried in vacuum for ~1-2 hrs at room temperature.

Form B of Compound A—Preparation Method 10

To a reactor vessel were sequentially charged compound A (mixture of polymorphs), water (2.0 V), and IPA (4.0 V). The resulting slurry was heated to 75° C. to form a solution. IPA (8.0 V) was then slowly charged over 90 minutes while maintaining the temperature at 70-75° C. During this time, compound A crystallized from solution. The slurry was cooled to ambient temperature over 3 h and aged at ambient temperature for a further 50 h. The solids were collected by filtration, washed with IPA (2.0 V), and dried under vacuum at 40° C. to provide Form B of compound A in 82% yield.

Table 2, supra, is reproduced below and sets forth the X-ray diffraction peaks observed for Form B of compound A.

TABLE 2

XRPD Peak Positions for Form B of Compound A.

| Pos. [°2θ] | d-spacing [Å] | Rel. Int. [%] |
| --- | --- | --- |
| 5.0 | 17.79192 | 56.67 |
| 5.6 | 15.84291 | 27.64 |
| 6.2 | 14.16750 | 56.60 |
| 7.3 | 12.11387 | 1.29 |
| 8.5 | 10.39085 | 15.91 |
| 11.2 | 7.93259 | 4.90 |
| 12.5 | 7.09034 | 5.45 |
| 13.5 | 6.54504 | 6.60 |
| 14.9 | 5.94738 | 7.79 |
| 15.2 | 5.81272 | 57.62 |
| 15.8 | 5.62075 | 25.30 |
| 15.9 | 5.55836 | 28.07 |
| 16.3 | 5.42768 | 7.96 |
| 16.7 | 5.29724 | 28.92 |
| 17.2 | 5.16239 | 47.38 |
| 17.5 | 5.08070 | 100.00 |
| 17.8 | 4.99676 | 55.49 |
| 18.6 | 4.77136 | 51.51 |
| 18.9 | 4.70370 | 12.08 |
| 20.1 | 4.42463 | 4.58 |
| 20.5 | 4.33118 | 42.34 |
| 20.8 | 4.27546 | 20.03 |
| 21.0 | 4.22175 | 16.50 |
| 21.8 | 4.07643 | 14.81 |
| 22.3 | 3.98920 | 20.06 |
| 22.8 | 3.89446 | 20.78 |
| 23.9 | 3.72765 | 6.29 |
| 24.0 | 3.70144 | 7.86 |
| 24.4 | 3.64301 | 13.63 |
| 25.1 | 3.54860 | 14.27 |
| 25.5 | 3.49056 | 16.11 |
| 25.7 | 3.46934 | 13.54 |
| 27.3 | 3.26880 | 6.08 |
| 28.2 | 3.16194 | 18.51 |
| 28.6 | 3.11881 | 2.62 |
| 30.2 | 2.95839 | 5.60 |
| 30.7 | 2.90800 | 15.69 |
| 31.5 | 2.84376 | 2.75 |
| 31.8 | 2.81261 | 14.16 |
| 32.3 | 2.77431 | 25.65 |
| 32.9 | 2.72628 | 3.13 |
| 33.2 | 2.69691 | 4.85 |
| 33.5 | 2.67365 | 7.08 |
| 34.1 | 2.62624 | 6.69 |
| 34.7 | 2.58345 | 6.04 |
| 35.8 | 2.50835 | 6.32 |
| 36.4 | 2.46997 | 2.39 |
| 36.9 | 2.43571 | 2.52 |
| 37.9 | 2.37271 | 4.64 |
| 38.8 | 2.32345 | 2.55 |
| 40.0 | 2.25278 | 6.92 |
| 41.1 | 2.19506 | 0.97 |
| 41.7 | 2.16684 | 2.73 |
| 42.5 | 2.12870 | 1.74 |
| 43.6 | 2.07769 | 2.05 |
| 44.3 | 2.04573 | 0.93 |

FIG. 4 depicts an XRPD pattern of Form B of compound A.

Figure 5:
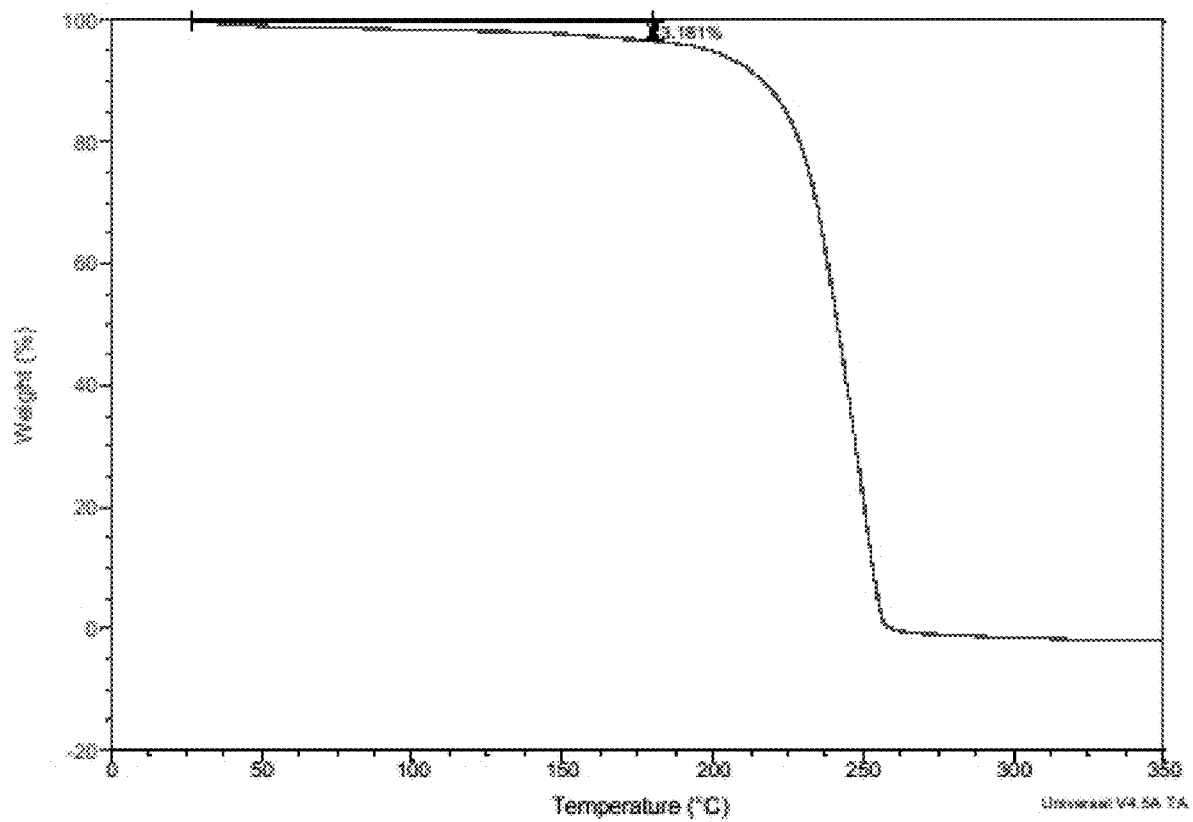
FIG. 5 depicts a TGA trace of Form B of compound A.

FIG. 5 depicts a DSC trace of Form B of compound A.

Figure 6:
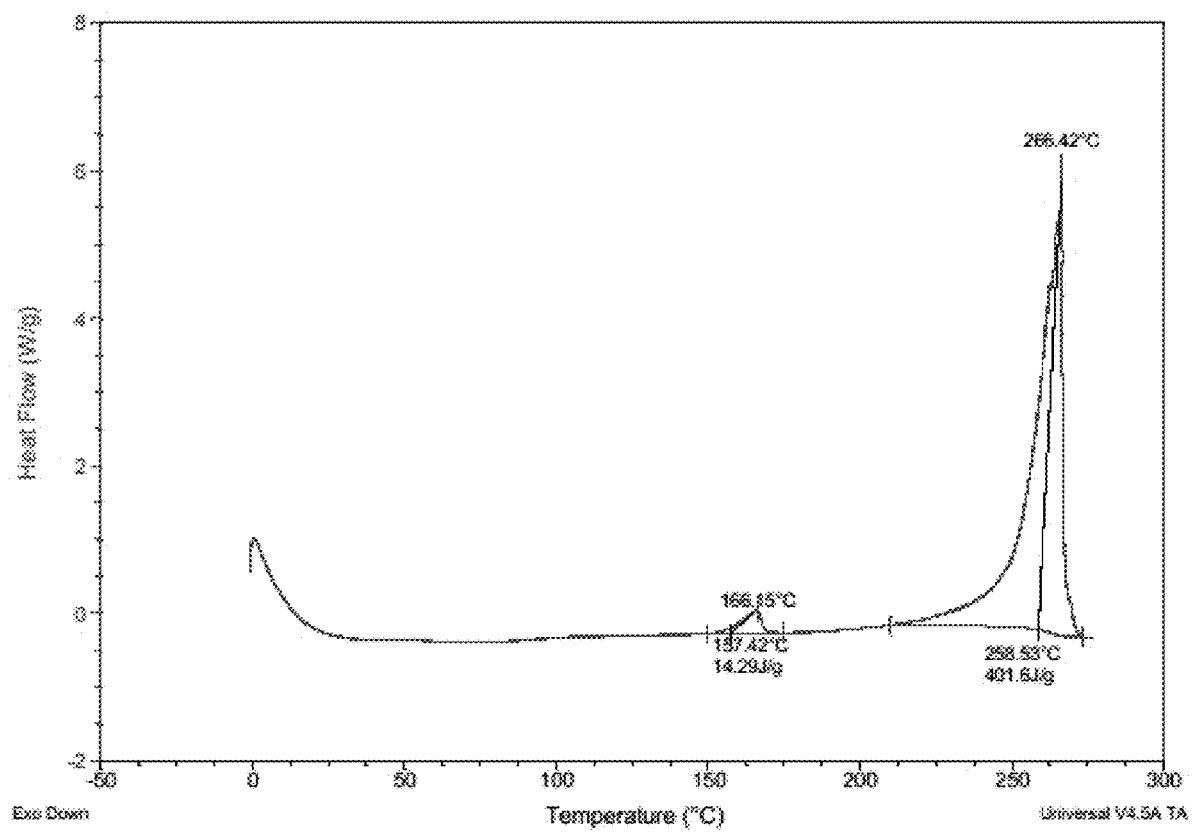
FIG. 6 depicts a DSC trace of Form B of compound A.

FIG. 6 depicts a TGA trace of Form B of compound A.

Example 3—Preparation of Free Base Form C of Compound A

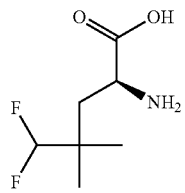

Form C of Compound A

Form C of compound A was prepared as described below.

Form C of Compound A—Preparation Method 1

Saturated solutions of compound A were set up in 3 solvents (water, methanol and acetone) and filtered through 0.45 m PTFE filters. Portions (~1.5 mL) of the prepared solutions were placed in an environment rich in methyl t-butyl ether (MTBE) coupled with the selected solvents on the basis of their boiling point difference. Solutions were visually inspected periodically for solid formation. Solids were isolated by surnatant removal and dried for about 1 hr in vacuum at room temperature.

Form C of Compound A—Preparation Method 2

Prolonged drying of Form B of compound A produced according to Preparation Method 1 (of Form B of compound A) in an oven at 40° C. yielded Form C.

Table 3, supra, is reproduced below and sets forth the X-ray diffraction peaks observed for Form C of compound A.

TABLE 3

XRPD Peak Positions for Form C of Compound A.

| Pos. [°2θ] | d-spacing [Å] | Rel. Int. [%] |
|---|---|---|
| 7.0 | 12.62256 | 100.00 |
| 9.0 | 9.84758 | 0.61 |
| 12.7 | 6.95918 | 1.03 |
| 13.7 | 6.45156 | 1.18 |
| 14.0 | 6.31699 | 1.35 |
| 14.6 | 6.06056 | 1.01 |
| 15.2 | 5.82154 | 12.92 |
| 16.1 | 5.50413 | 26.10 |
| 16.3 | 5.44751 | 81.62 |
| 17.1 | 5.19272 | 8.97 |
| 18.1 | 4.90525 | 15.44 |
| 18.6 | 4.76865 | 13.36 |
| 19.3 | 4.59577 | 19.92 |
| 19.5 | 4.54539 | 23.36 |
| 20.6 | 4.31976 | 8.55 |
| 21.1 | 4.20763 | 13.52 |
| 22.2 | 3.99811 | 6.29 |
| 22.7 | 3.92968 | 2.23 |
| 23.2 | 3.83507 | 4.95 |
| 24.1 | 3.68762 | 4.52 |
| 24.7 | 3.60895 | 3.78 |
| 25.1 | 3.54244 | 18.19 |
| 25.6 | 3.47585 | 2.91 |
| 26.1 | 3.40952 | 1.00 |
| 27.2 | 3.27682 | 2.65 |
| 27.7 | 3.22347 | 2.42 |
| 28.3 | 3.15590 | 2.86 |
| 30.0 | 2.98309 | 1.88 |
| 30.7 | 2.90868 | 2.28 |
| 31.5 | 2.84434 | 1.49 |
| 32.6 | 2.74884 | 6.13 |
| 32.8 | 2.72865 | 4.39 |
| 33.9 | 2.64294 | 3.65 |
| 34.5 | 2.59799 | 2.31 |
| 35.2 | 2.55115 | 2.01 |
| 35.6 | 2.51855 | 3.22 |
| 36.3 | 2.47209 | 1.77 |
| 36.8 | 2.44270 | 0.54 |
| 37.3 | 2.41347 | 2.40 |
| 37.7 | 2.38315 | 1.76 |
| 39.5 | 2.28084 | 0.13 |
| 40.1 | 2.24833 | 1.26 |
| 40.6 | 2.22413 | 0.93 |
| 41.9 | 2.15718 | 0.57 |
| 42.3 | 2.13551 | 0.66 |
| 42.8 | 2.11132 | 0.79 |
| 43.9 | 2.06411 | 0.76 |

FIG. 7 depicts an XRPD pattern of Form C of compound A.

Figure 8:
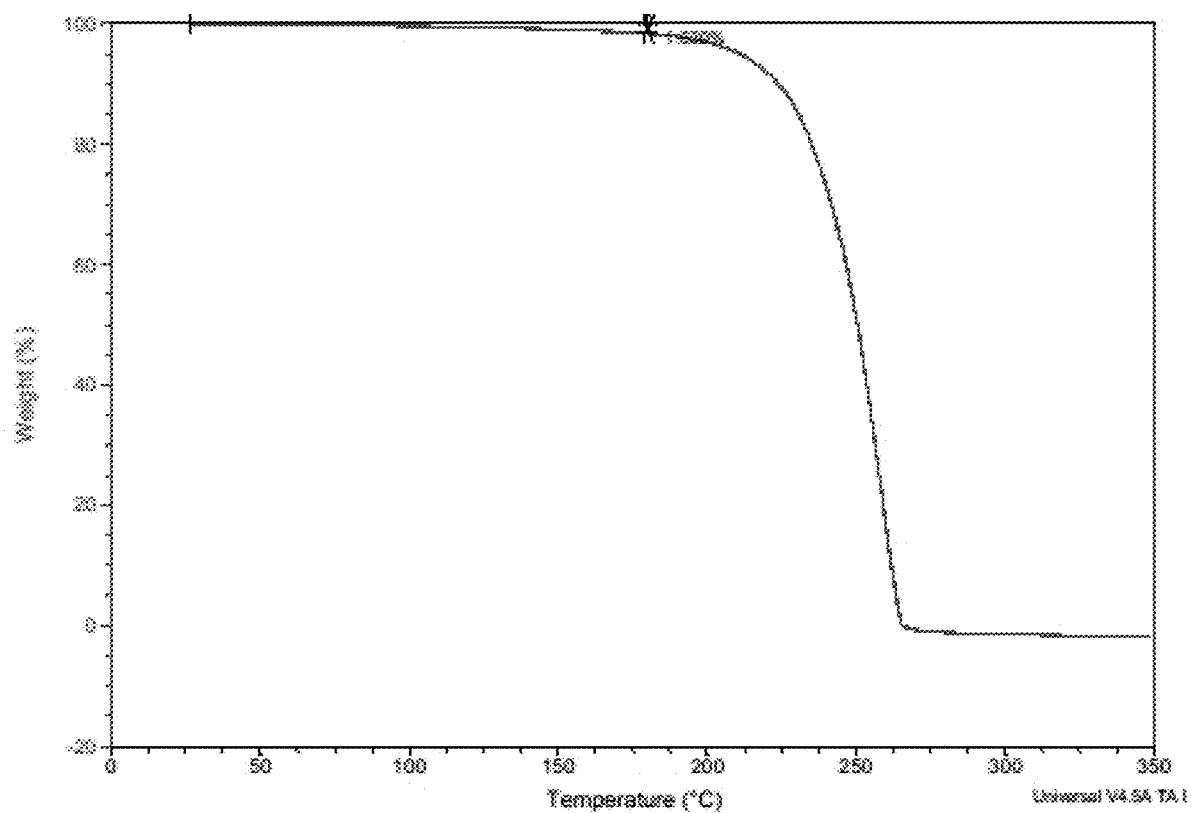
FIG. 8 depicts a TGA trace of Form C of compound A.

FIG. 8 depicts a DSC trace of Form C of compound A.

Figure 9:
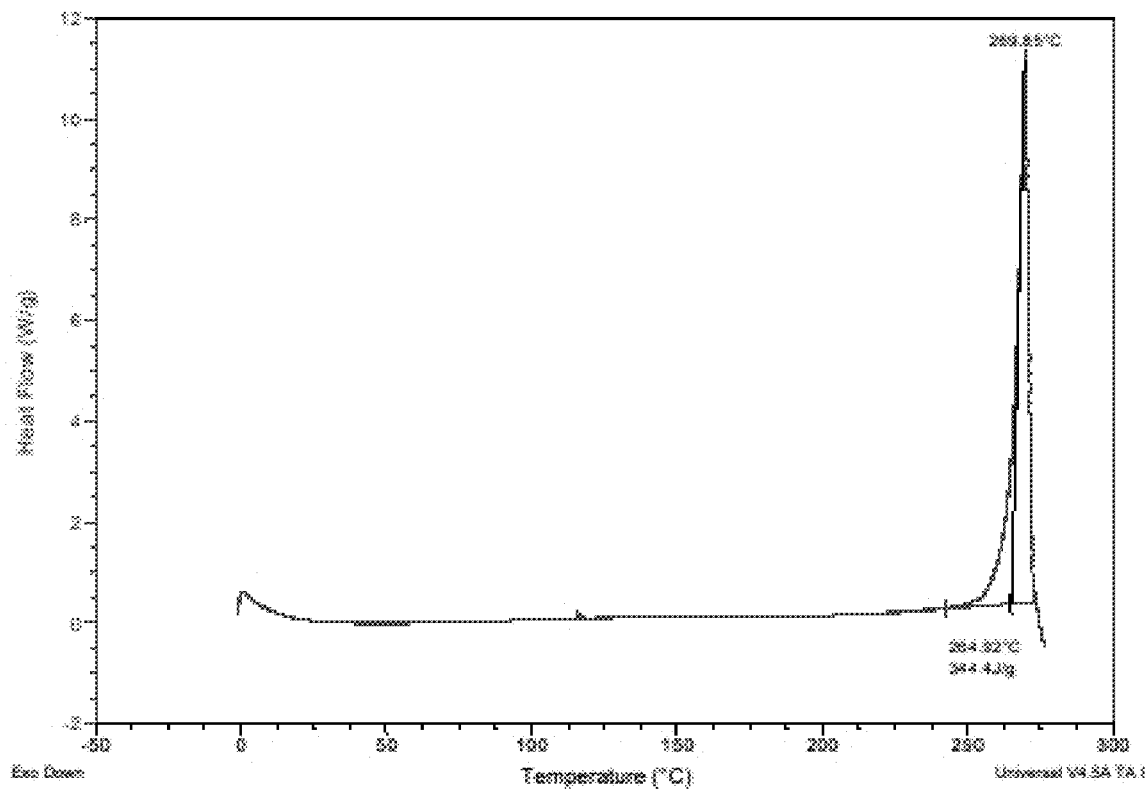
FIG. 9 depicts a DSC trace of Form C of compound A.

FIG. 9 depicts a TGA trace of Form C of compound A.

Example 4—Single Crystal Studies of Form A of Compound 1

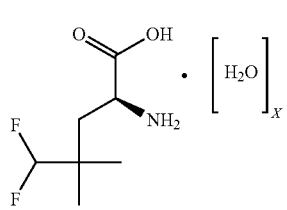

wherein x is about ¾.

Form A of compound 1 was prepared as follows. Compound A, 40 mg (0.3 mmol) was dissolved in 5 mL of deionized water and evaporated on a hot plate until needle-like crystals emerged from the hot solution. The crystals were transferred into another vial and capped.

These crystals were suitable for X-ray diffraction. The crystals were observed to be thin, long "needle" like crystals and X-ray diffraction analysis was carried out at room temperature with Cu irradiation. Diffraction was seen, a unit cell was obtained, and a powder pattern was simulated. During the measurement at room temperature, however, it was observed that there was a decay in the intensities, and after about 30 minutes the crystallinity was significantly lost and a full data set could not be determined.

To avoid loss of crystallinity, new crystals were prepared as described above and X-ray diffraction analysis of the new crystals was carried out at low temperature (about 250 K, inert gas stream). Under these conditions, a full data set was determined and the structure was solved and refined.

Single crystal studies of Form A of compound 1 produced a chiral monoclinic P2₁ unit cell with the parameters shown below in Table 11.

TABLE 11

Unit Cell Parameters for Single Crystal of Compound 1

| a | 5.9045(6)Å |
| b | 30.326(3) Å |

TABLE 11-continued

| Unit Cell Parameters for Single Crystal of Compound 1 | |
|---|---|
| c | 10.505(1) Å |
| V | 1880.7(3) Å$^3$ |
| β | 90.93(3)° |
| $R_1(I > 2\sigma(I))$ | 5.78% |
| GooF (5) | 1.052 |
| $wR_2$ (all data) | 14.63% |

Figure 10:
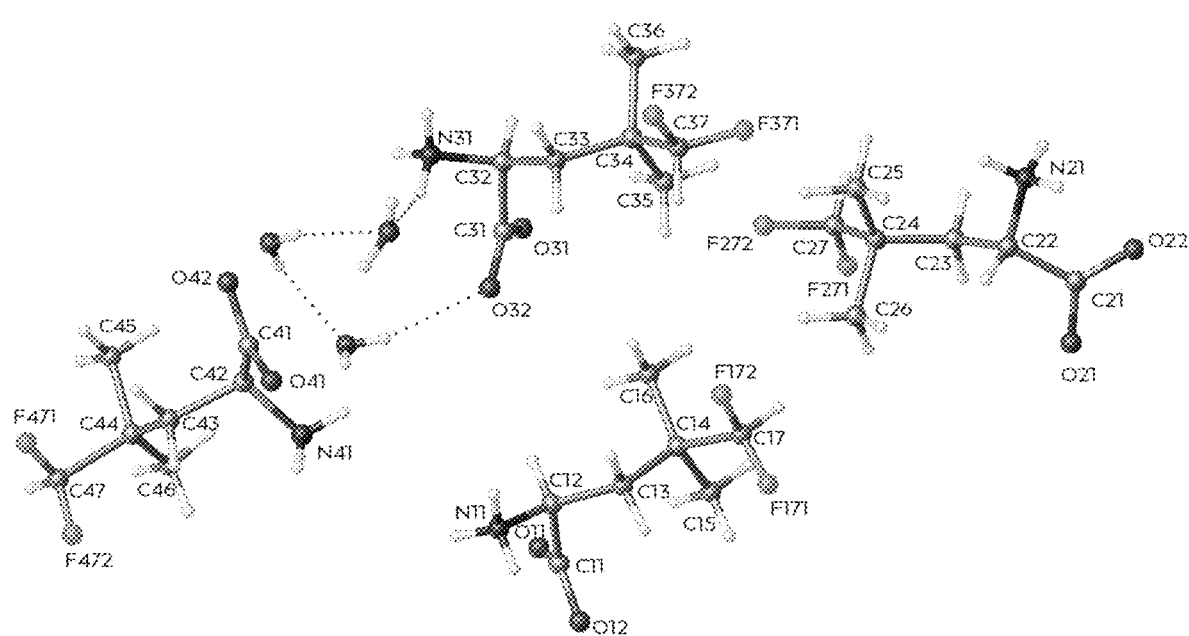
FIG. 10 depicts a unit cell of Form A of compound 1.

FIG. 10 shows the asymmetric unit, whereby chiral centers are found at the carbon atoms labeled as C12, C22, C32, and C42, respectively. The absolute configuration of Form A of compound 1 was determined to be S for the molecules present in the unit cell.

The unit cell was observed to be asymmetric and includes 4 independent molecules of compound A and 3 full occupied water molecules. The cell volume of 1880.7(3) Å$^3$ corresponds to 8 molecules of compound A and 6 water molecules in the unit cell. The molecular formula can be described as $[C_7H_{13}F_2N_1O_2]_4 \cdot [H_2O]_3$, where the $[C_7H_{13}F_2N_1O_2]$ entity is a zwitter ion.

The data set described above obtained at low temperature was used with the unit cell data set described above obtained at room temperature. The unit cell found at room temperature is a=5.90 A, b=30.34 A, c=10.51 A; b=90.78°, which is comparable to the unit cell found at 250 K.

Crystallographic software (e.g., Mercury Program 3.10.1 (Build 168220)), was used to simulate the XRPD pattern shown in FIG. 11. Table 4, supra, is reproduced below and sets forth the X-ray diffraction peaks for Form A of compound 1.

TABLE 4

| XRPD Peak Positions for Form A of Compound 1. | |
|---|---|
| Pos. [°2θ][1] | Rel. Int. [%] |
| 5.8 | 4.68662 |
| 8.4 | 8.38368 |
| 8.9 | 7.88716 |
| 10.2 | 22.3888 |
| 12.1 | 12.5225 |
| 15.2 | 5.87649 |
| 16.9 | 33.4848 |
| 17.1 | 100 |
| 17.3 | 69.1395 |
| 17.4 | 10.2511 |
| 17.6 | 51.5098 |
| 17.9 | 17.534 |
| 18.1 | 20.8017 |
| 18.3 | 92.648 |
| 19 | 5.66529 |
| 19.4 | 7.89022 |
| 20.6 | 18.3548 |
| 20.7 | 43.0262 |
| 20.8 | 4.93037 |
| 20.9 | 25.1766 |
| 22.2 | 13.6118 |
| 22.4 | 4.72072 |
| 23.4 | 28.7398 |
| 23.5 | 17.6636 |
| 24.5 | 10.0399 |
| 25.4 | 9.69082 |
| 25.5 | 4.9819 |
| 26.1 | 23.8361 |
| 26.7 | 5.4164 |
| 26.8 | 5.28821 |
| 26.9 | 5.25375 |
| 27.2 | 16.7917 |
| 28 | 5.88228 |
| 29.4 | 16.6576 |
| 30.4 | 16.3391 |

TABLE 4-continued

| XRPD Peak Positions for Form A of Compound 1. | |
|---|---|
| Pos. [°2θ][1] | Rel. Int. [%] |
| 31.8 | 5.88242 |
| 32.8 | 11.489 |
| 33.6 | 11.3981 |
| 35 | 11.5181 |
| 35.1 | 7.77114 |
| 35.2 | 4.51035 |
| 35.7 | 5.72326 |
| 37 | 17.492 |
| 38.3 | 7.4528 |
| 38.8 | 4.79161 |
| 39.6 | 4.56053 |
| 40.6 | 6.02793 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:

1. A crystalline form of compound A:

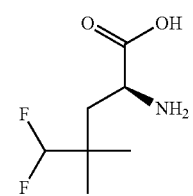

wherein the crystalline form is selected from the group consisting of Form A of compound A, Form B of compound A, and Form C of compound A; and wherein:

Form A of compound A is characterized by peaks in its XRPD pattern at about 4.4, about 16.2, about 17.3, about 17.5, and about 17.7 degrees 2-theta;

Form B of compound A is characterized by peaks in its XRPD pattern at about 5.0, about 6.2, about 15.2, about 17.5 and about 17.8 degrees 2-theta; and Form C of compound A is characterized by peaks in its XRPD pattern at about 7.0, about 16.1 about 16.3, about 19.3, and about 19.5 degrees 2-theta.

2. The crystalline form according to claim 1, wherein said crystalline form is Form A of compound A having at least about 95% by weight of Form A of compound A.

3. The crystalline form according to claim 1, wherein said crystalline form is Form A of compound A having at least about 99% by weight of Form A of compound A.

4. The crystalline form according to claim 1, wherein said crystalline form is Form A of compound A.

5. The crystalline form according to claim 1, wherein said crystalline form is Form A of compound A having the XRPD pattern as depicted in FIG. 1 wherein each peak is within +/−0.2 degrees 2-theta.

6. The crystalline form according to claim 1, wherein said crystalline form is Form B of compound A.

7. The crystalline form according to claim 1, wherein said crystalline form is Form B of compound A having the XRPD pattern as depicted in FIG. 4 wherein each peak is within +/−0.2 degrees 2-theta.

8. The crystalline form according to claim 1, wherein said crystalline form is Form C of compound A.

9. The crystalline form according to claim 1, wherein said crystalline form is Form C of compound A having the XRPD pattern as depicted in FIG. 7 wherein each peak is within +/−0.2 degrees 2-theta.

10. A composition comprising the crystalline form according to claim 1 and a pharmaceutically acceptable carrier or excipient.

11. The crystalline form according to claim 1, wherein said crystalline form is Form B of compound A having at least about 95% by weight of Form B of compound A.

12. The crystalline form according to claim 1, wherein said crystalline form is Form B of compound A having at least about 99% by weight of Form B of compound A.

13. The crystalline form according to claim 1, wherein said crystalline form is Form C of compound A having at least about 95% by weight of Form C of compound A.

14. The crystalline form according to claim 1, wherein said crystalline form is Form C of compound A having at least about 99% by weight of Form C of compound A.

15. The composition of claim 10, wherein the crystalline form is Form A of compound A.

16. The composition of claim 10, wherein the crystalline form is Form B of compound A.

17. The composition of claim 10, wherein the crystalline form is Form C of compound A.

\* \* \* \* \*